United States Patent [19]
Baba et al.

[11] Patent Number: 5,949,811
[45] Date of Patent: Sep. 7, 1999

[54] X-RAY APPARATUS

[75] Inventors: Rika Baba, Kokubunji; Ken Ueda, Oume; Hironori Ueki, Kokubunji; Akira Kuba, Nagareyama; Ken Ishikawa, Matsudo; Takashi Ishiguro, Kita-ku, all of Japan

[73] Assignee: Hitachi Medical Corporation, Tokyo, Japan

[21] Appl. No.: 08/947,156

[22] Filed: Oct. 8, 1997

[30] Foreign Application Priority Data

Oct. 8, 1996 [JP] Japan .................................. 8-267518
Jan. 14, 1997 [JP] Japan .................................. 9-004986

[51] Int. Cl.$^6$ ...................................................... A61B 6/00
[52] U.S. Cl. ........................................... 375/108; 378/97
[58] Field of Search .............................. 378/97, 106, 108, 378/109, 110, 111, 112, 114, 115, 116

[56] References Cited

U.S. PATENT DOCUMENTS

| 4,639,943 | 1/1987 | Heinze et al. | 378/96 |
| 5,396,532 | 3/1995 | Aichinger et al. | 378/112 |
| 5,400,378 | 3/1995 | Toth | 378/16 |
| 5,617,462 | 4/1997 | Spratt | 378/98.7 |

FOREIGN PATENT DOCUMENTS

| 53-126291 | 11/1978 | Japan . |
| 57-88698 | 6/1982 | Japan . |
| 62-15800 | 1/1987 | Japan . |
| 4-336045 | 11/1992 | Japan . |

OTHER PUBLICATIONS

JSRT, vol. 8, No. 45, p. 1014.

JAMIT Frontier, '95, "Cone–Beam CT Angiography", K. Sekihara et al, pp. 23–28.

"BME", vol. 33, theses of 34th meeting of Japan society of M"BME", vol. 33, theses of 34th meeting of Japan society of electromedica 62, 1994, No. 1, pp. 19–22.

Large Area, Flat Panel, Amorphous Silicon Imagers, L. E. Antonuk et al, SPIE, vol. 2432, Physics of Medical Imaging, pp. 216–217.

Primary Examiner—David P. Porta
Attorney, Agent, or Firm—Fay, Sharpe, Beall, Fagan, Minnich & McKee

[57] ABSTRACT

An X-ray apparatus acquires an X-ray image of an object by radiating X-rays to the object and includes an X-ray radiator for radiating X-rays to an object. An imager acquires an X-ray image of the object and radiation dose controller controls the radiation dose so as to acquire an X-ray image having a predetermined X-ray relative noise level on the basis of an image level of a predetermined area in the X-ray image.

36 Claims, 19 Drawing Sheets

FIG. 4A
| | |
|---|---|
| mAs VALUE $Q_o$ | 1 [mAs] |
| CAMERA IRIS $\Omega_o$ | $4\pi$ [cm$^2$] |
| AMPLIFIER GAIN $G_o$ | 1 |
| STANDARD CAMERA MODE | TWO THOUSAND MODE |
| STANDARD I.I. MODE | 12 [inch] MODE |
| X-RAY EXPOSURE FIELD $A_o$ | 12 [inch] |
| AIR GAP $L_o$ | 5 [cm] |
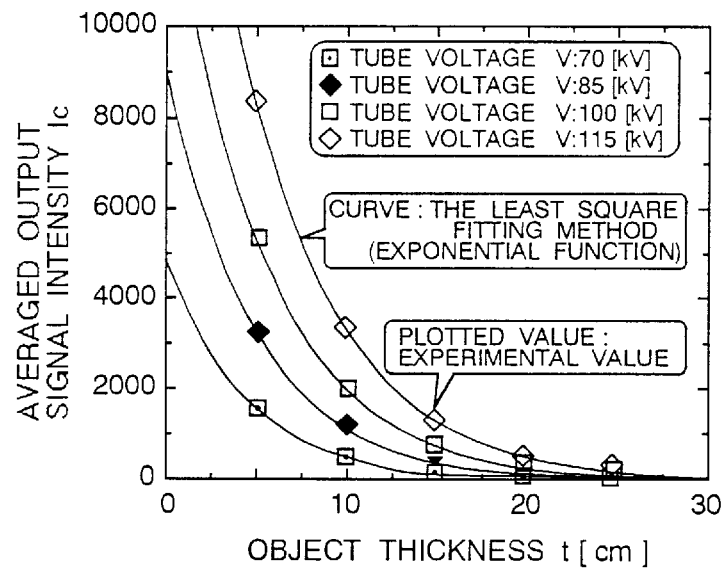
FIG. 4B
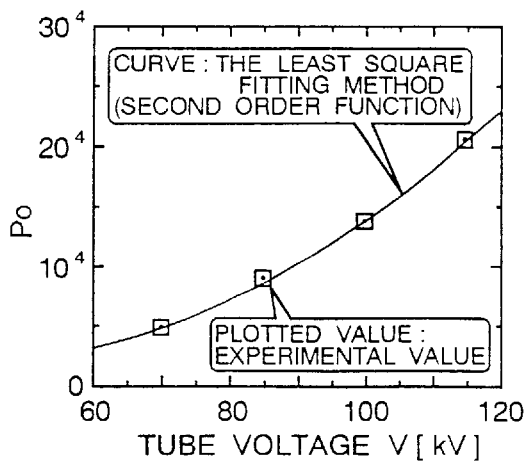
FIG. 4C
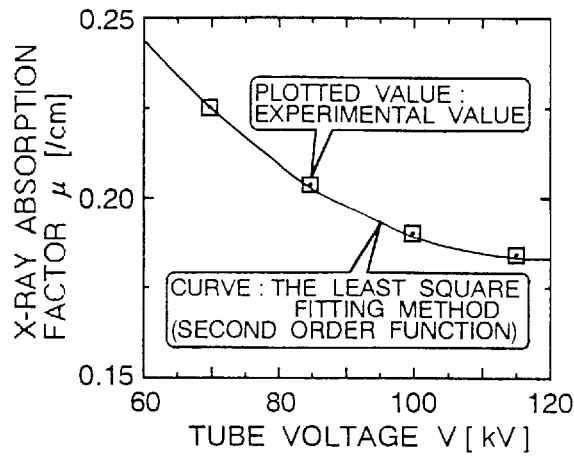
FIG. 4D

X-RAY APPARATUS

BACKGROUND OF THE INVENTION

1. Field of the Invention

The present invention relates to an X-ray apparatus, and more particularly, to a technique which is effectively applied to an exposure controller for properly controlling X-ray conditions at the time of radiographic exposure in X-ray diagnosis.

2. Related Background Art

A radiation dose control for properly setting X-ray conditions at the time of radiographic exposure is indispensable when an operation is shifted from fluoroscopic exposure to radiographic exposure or when a series of radiographic exposures are sequentially performed. An X-ray automatic exposure control method in an X-ray apparatus for shifting the operation from the fluoroscopic exposure to the radiographic exposure has been improved over a long time. However, proper setting of the X-ray conditions is difficult due to influences by contrast media, bones, and the like when X-rays are transmitted through the object. The method is strongly requested to be improved, especially in diagnosis of the digestive organs for which the method is often used.

As a conventional X-ray automatic exposure control method, for example, there is an X-ray automatic exposure controller described in Japanese Patent Application Laid-Open No. (JP-A) 57-88698.

The X-ray automatic exposure control apparatus detects partially picked up X-ray transmission images of an object by a plurality of photo-diodes, and radiation time of X-rays upon X-ray radiographic exposure is controlled on the basis of outputs of detectors of selected photo-diodes among the plurality of photo-diodes.

That is, since the X-ray automatic exposure controller can control, in a real time manner, the radiation time of X-rays upon the X-ray radiographic exposure on the basis of the output signals of the photo-diodes, the control of which is not influenced by individual difference of an object, the X-ray radiographic conditions, and the like can be performed.

As another X-ray automatic exposure control method, there is an X-ray diagnostic apparatus described in JP-A-62-15800.

The X-ray diagnostic apparatus obtains average thickness and the maximum and minimum thickness of an object from video signals outputted from an X-ray detector at the time of X-ray fluoroscopic exposure of the object, determines X-ray radiographic conditions so that the contrast of an X-ray radiographic image of the object becomes maximum, and controls the radiographic exposure.

That is, since the X-ray radiographic conditions of the object are determined by using the video signals outputted from the X-ray detector, since it is unnecessary to prepare photo-diodes which are required in the above-mentioned JP-A-57-88698 and the X-ray radiographic conditions can be controlled with a simple apparatus construction.

Generally, when the exposure control is performed by using the video signals, it is necessary to execute a control of radiographic exposure time in time scale shorter than a speed of reading the video signals. Therefore, a real-time control cannot be performed.

As described in the above-mentioned JP-A-62-15800, the X-ray radiographic conditions of the object have to be preliminarily determined.

Meanwhile, in the X-ray apparatus, it is desirable to suppress the dose of X-rays radiated to the object and to obtain a high-quality X-ray image, especially, in the radiographic exposure to a region (aimed field) in which an examiner is interested.

As a conventional X-ray apparatus, there is an X-ray fluoroscope radiographic apparatus in which an X-ray tube and a two-dimensional X-ray detector are used so as to face each other and fluoroscopic two-dimensional X-ray images of an object are obtained from various directions, and the radiographic two-dimensional X-ray images of an object is continuously obtained. There is also an X-ray rotatographic apparatus for continuously acquiring two-dimensional X-ray transmission images of an object while rotating an X-ray tube and a two-dimensional X-ray detector which are arranged so as to face each other around the object. These X-ray apparatus can display images acquired by the radiographic exposure in a real time manner and can continuously display the images after the radiographic exposure.

There is a cone-beam CT having the X-ray rotatographic apparatus as a measurement system and three-dimensional image reconstructing means as an image processing unit. The cone-beam CT can image three-dimensional distribution of absorption coefficients of the object from a series of acquired two-dimensional X-ray transmission images.

There is also an X-ray CT which has a one-dimensional X-ray detector or a detector array comprising a plurality of one-dimensional detectors and acquires one or a plurality of X-ray slice images at once. In the X-ray CT, however, it is necessary to repeatedly execute measurement in order to image the three-dimensional distribution of the absorption coefficients. On the contrary, the cone-beam CT can collect the two-dimensional transmission images for reconstructing a number of X-ray slice images at once and is therefore characterized in that a three-dimensional image can be acquired in shorter time.

For example, such a cone-beam CT is disclosed in "JAMIT Frontier '95" p. 23–28, which uses a detector having an X-ray image intensifier, an optical lens system, and a television camera as a two-dimensional X-ray detector. There is also a cone-beam CT using a detector having a fluorescent screen, an optical lens system, and a television camera as a two-dimensional X-ray detector disclosed in "BME" Vol. 33, special edition (theses of the 34th meeting of Japan society of ME) p. 109.

The two-dimensional X-ray detector has, however, a narrower dynamic range as compared with that of a one-dimensional X-ray detector used for the X-ray CT, so that a minute difference of the dose of X-ray entering the detector cannot be detected by a measurement system. The contrast resolution of measurement data of the two-dimensional X-ray detector is consequently lower than that of the one-dimensional X-ray detector. The contrast resolution of a three-dimensional image obtained by the cone-beam CT is therefore inferior to that obtained by a CT having the one-dimensional X-ray detector. Consequently, in the conventional cone-beam CT, an image cannot be obtained under conditions where absorption of X-rays by an object is large and an X-ray transmitted rate is small, so that there is a drawback that the maximum object thickness for obtaining an image is small.

On the other hand, the radiographic conditions in case of performing the rotatographic exposure by using the two-dimensional X-ray detector can be principally set to the same as those of a general X-ray CT. In the rotatographic exposure using the two-dimensional detector, as a conventional technique for increasing the maximum object thickness for obtaining an image by improving the contrast resolution for the object having small X-ray transmitted rate, it is considered to use automatic exposure control means which is generally used for controlling X-ray dose in X-ray fluoroscopy. That is, when the absorption of X-rays by the object is large, the X-ray dose is automatically increased to improve the level of an image, thereby compensating the narrowness of the dynamic range of the detector.

An X-ray apparatus using the automatic exposure control means is disclosed, for example, in JSRT No. 45, Vol. 8, p 1014. According to the X-ray apparatus, an optical sensor is mounted in an optical lens system constructing a two-dimensional X-ray detector, the average brightness of an arbitrary aimed region on an output fluorescent face of an X-ray image intensifier is measured by the optical sensor, and an X-ray tube voltage is controlled so that an output level of the optical sensor becomes constant.

In case of applying the idea of the automatic exposure control means to a rotatographic apparatus or a cone-beam CT, when the thickness of the object is increased at a predetermined rotation angle and the X-ray absorption of the aimed region is increased, the output level of the optical sensor decreases. By automatically executing a control to increase the X-ray tube voltage in order to compensate the decrease in the output of the optical sensor, the dose of X-ray radiated from the X-ray tube is increased, and as a result, the level of the image is raised. The narrowness of the dynamic range of the two-dimensional X-ray detector can be consequently compensated.

A general X-ray CT in which X-ray dose is changed at each exposure angle in order to reduce the dose of X-rays radiated to an object is described in JP-A-53- 126291. In the X-ray CT, X-ray radiographic exposure is performed to an object as a preliminary measurement. The shape of a slice or information (X-ray absorption information) regarding the X-ray absorption of the object is preliminarily formed on the basis of the acquired X-ray image. In the measurement, by controlling applying time of a voltage which is applied to the X-ray tube on the basis of the slice shape or the X-ray absorption information, the dose of X-rays entering the detector is kept constant.

The inventors of the present invention examined the conventional techniques regarding the automatic exposure control in which operation is shifted from the fluoroscopic exposure to the radiographic exposure and found out the following problems.

In the X-ray automatic exposure control apparatus described in JP-A-57-88698, since a number of photo-diodes are necessary for performing an accurate exposure control, there is a problem that costs are high.

Since a controller for controlling the number of photo-diodes and also the exposure on the basis of a number of inputs is more complicated as the number of photo-diodes increases, there is a problem that the costs further increase.

Further, since the photo-diode and the X-ray detector have different sensitivity characteristics to light, there is a problem that the difference makes an accurate exposure control difficult.

On the other hand, with respect to X-ray scattering which occurs when X-rays are transmitted through an object, it is known that intensity and distribution of the scattered X-ray are changed generally by a tube voltage of an X-ray tube, the kind of an X-ray filter, the thickness of the object, a distance between the object and an input face of the X-ray detector (hereinbelow, referred to as an "air gap"), the kind of an X-ray grid, and the like and the X-ray scattering is also influenced by the size of an X-ray exposing area.

In an apparatus using an X-ray image intensifier (hereinbelow, described as an "X-ray I. I.") as a detector, it is known that veiling glare occurring when an X-ray image is converted into an optical image changes the intensity and distribution of the scattered X-ray in accordance with an I. I. mode which specifies a detection area.

In an apparatus using the X-ray I. I. and a television camera, therefore, in addition to primary X-ray and scattered X-ray entering the X-ray I. I., the result also including the veiling glare occurring in the X-ray I. I. is picked up by the television camera, that is, converted into video signals.

In the X-ray diagnostic apparatus described in JP-A-62-15800, when the exposure control is executed by using the video signals, since influence by the X-ray scattering and the veiling glare is not considered, accurate thickness of the object cannot be obtained. Consequently, there is a problem that X-ray radiographic conditions cannot be accurately determined.

The inventors of the present invention examined the conventional techniques regarding the continuous radiography and found out the following problems.

In the measurement system for rotatography used for the cone-beam CT, in order to improve the S/N ratio of the three-dimensional image of the aimed region for the same X-ray dose sum, the distribution of the X-ray dose and the image level have to be adjusted. The X-ray dose sum denotes a sum of X-ray dose used for the radiographic exposure at every angle in a series of rotatographic exposures.

In each of the rotatographic apparatus, the cone-beam CT, and the X-ray CT described in JP-A-53-126291 each having the automatic exposure control means, when one X-ray image is acquired, it is the goal to acquire the X-ray image having picture quality as high as possible. That is, in the conventional X-ray apparatus, since the distribution of the X-ray dose is not adjusted so that the S/N ratio of the three-dimensional image of the aimed area is proper for the same X-ray dose sum, there is a problem that the contrast resolution of a three-dimensional reconstructed image cannot be further improved. Another problem is that the dose of X-rays radiated to the object cannot be further reduced.

With respect to the fluoroscopic or continuous exposure, in the automatic exposure control having the logic of increasing or decreasing the X-ray dose in correspondence to change with time in the characteristics of the object, there is a problem such that when the X-ray tube voltage changes, the image contrast of the same region of the object varies.

In the measurement system of the X-ray apparatus, the X-ray dose has to be properly set at each exposure angle and the image signal level has to be adjusted in order to maximally use the dynamic range of the detector according to the set X-ray dose. In order to adjust the image signal level, it is desirable to adjust a camera input light level by adjusting an optical iris in the optical system.

A digital X-ray radiographic apparatus having a mechanism of adjusting the camera input light level is described in JP-A-4-336045. According to the digital X-ray radiographic apparatus, the radiation dose of X-rays is controlled by the above-mentioned automatic exposure control. The amount of light entering the television camera is adjusted by providing an iris mechanism in front of the television camera and controlling the iris mechanism. Specifically, the control method adjusts the iris on the basis of the ratio of the maximum level of the video signal as an output of the television camera to a peak level of the video signal. In the digital X-ray radiographic apparatus, however, since the control of the dose of X-rays radiated to the object and the control of the amount of light entering the television camera are separately performed, the dynamic range of an analog to digital (AD) converter for converting the X-ray image into digital signals can be maximally used. However, the problem regarding the automatic exposure control cannot be solved. The invention of the digital X-ray radiographic apparatus is therefore different from the present invention.

When the X-ray tube voltage is changed, the X-ray energy spectrum, that is, X-ray quantum energy distribution is changed. When the X-ray tube voltage increases, the average level of the X-ray quantum energy increases. As a result, the X-ray absorption coefficient of an object region of the object or a background region is generally reduced and the ratio of the X-ray absorption coefficient of the object region to that of the background region is changed. The absorption coefficients obtained by three-dimensional reconstruction are, therefore, inaccurate and vary according to position. Consequently, variance of the image is increased and there is a problem that the contrast resolution deteriorates as compared with a case of controlling the X-ray dose while the tube voltage is constant.

SUMMARY OF THE INVENTION

A main object of the invention is, therefore, to provide an X-ray apparatus which can properly set X-ray conditions upon radiographic exposure.

It is a first object of the invention to provide an X-ray apparatus which can determine radiographic conditions that make output level of X-ray radiographic images proper in short time when the X-ray radiographic conditions are determined from X-ray fluoroscopic conditions.

Another object of the invention is to provide an X-ray apparatus which can determine radiographic conditions in which influence by X-ray scattering is considered when X-ray radiographic conditions are determined from X-ray fluoroscopic conditions.

Further another object of the invention is to provide a technique which can realize an X-ray apparatus at low costs with a simple apparatus construction.

It is a second object of the invention to provide a technique which can distribute X-ray dose so that the S/N ratio of a three-dimensional image of an aimed area of an object increases for the same X-ray dose sum.

Another object of the invention is to provide a technique which can reduce the dose of X-rays radiated to an object.

Further another object of the invention is to provide a technique which can maximally use a limited dynamic range of a two-dimensional X-ray detector in a measurement system having the two-dimensional X-ray detector and can compatibly perform settings of both of the X-ray dose and the image level.

Further another object of the invention is provide an X-ray apparatus which can improve contrast resolution of an X-ray image.

According to the fundamental feature of the invention, the main object is realized by an X-ray apparatus having means for controlling radiation dose of X-rays just after fluoroscopic exposure on the basis of image level of a predetermined area in an X-ray image acquired just before when operation is shifted from X-ray fluoroscopic exposure to X-ray radiographic exposure or during a series of fluoroscopic exposures.

With respect to the first object of the invention, outlines of representative techniques among techniques disclosed in the application and drawings will be briefly described as follows.

1) For example, upon shipment from a factory, the relation of an output level of X-ray detection means, a tube voltage of an X-ray tube, and the thickness of an object which is preliminarily measured with respect to a plurality of X-ray filters, a plurality of X-ray grids, or combination of the plurality of X-ray filters and the plurality of X-ray grids in a state where a mAs value of the X-ray tube, an X-ray exposing area, a distance between the object and an input face of the X-ray detection means, and a gain of the X-ray detection means are set to predetermined values, respectively, is stored as a first function in storage means.

Further, as a second function, preliminarily measured ratio of change in the output level of the X-ray detection means when change amounts of the X-ray exposing area and the distances from the object to the input face of the X-ray detection means for predetermined values are set to variables with respect to the plurality of X-ray filters, the plurality of X-ray grids, or the combination of the plurality of X-ray filters and the plurality of X-ray grids is stored in the storage means.

At the time of operation, that is, the fluoroscopic exposure, the fluoroscopic exposure is executed under the fluoroscopic conditions based on setting conditions set by the operator or the automatic exposure control for fluoroscopy and an imaging region of the object is determined.

When operation is shifted from the fluoroscopic exposure to the radiographic exposure, radiographic conditions calculation means calculates radiographic conditions from the output level of the detection means upon the fluoroscopic exposure, the fluoroscopic conditions, and the first and second functions, and control means controls the radiographic conditions such as the tube voltage and the mAs value of the X-ray tube, the gain of the X-ray detection means, and the like on the basis of the radiographic conditions. Consequently, the X-ray radiographic exposure can be performed under the radiographic conditions that make output level of X-ray radiographic images proper in short time.

Since the relation between the X-ray exposing area, and the distance from the object to the input face of the X-ray detection means, and the output level of the detection means, that is, the influence on the output level of the detection means exerted by the X-ray scattering is considered in the second function, the X-ray image of the object under the radiographic conditions in which the influence by the X-ray scattering is considered can be acquired.

2) The radiographic conditions calculation means approximates the output level of the detection means by the product of the ratio of the mAs value of the X-ray tube and the gain of the X-ray detection means to the predetermined values and the first and second functions, and calculates the X-ray radiographic conditions from the X-ray fluoroscopic conditions, the output level of the X-ray detection means calculated by the product, and the output level of the X-ray detection means at the time of the fluoroscopic exposure. Therefore, the X-ray radiographic exposure can be performed under the radiographic conditions that make output level of X-ray radiographic images proper with little arithmetic operation amount, that is, in short time.

Since the output level of the X-ray detection means at the time of the radiographic exposure can be determined only by the product arithmetic operation, a cheap apparatus which does not have high-speed calculation ability can be used. The X-ray apparatus can be, therefore, realized at low costs.

3) Since the second function peculiar to each apparatus can be determined by approximating the second function by the product of a simpler third function showing the ratio of change in the output level at the x-ray detection means when the change amount of the x-ray exposing area for the predetermined value is set to a variable and a fourth function showing the ratio of change in the output level of the x-ray detection means when the change amount of the distance from the object to the input face of the x-ray detection means for the predetermined value is set to a variable, for example, there is an effect that measurement for adjustment of an apparatus or the like can be executed in short time.

4) Since the measurement of the change amount of the X-ray exposing area for the predetermined value can be omitted by setting the third function to a predetermined value, namely, by approximating the third function by a predetermined value, a measurement mechanism for measuring the change amount of the X-ray exposing area can be omitted.

Therefore, the X-ray apparatus can be cheaply manufactured.

5) By setting the fourth function to a predetermined value, that is, by approximating the fourth function by a predetermined value, measurement for setting the distance from the object to the input face of the X-ray detection means for the predetermined value to a variable can be omitted, a measurement mechanism for measuring the output level of the X-ray detection means when the distance from the object to the input face of the X-ray detection means is varied can be omitted.

Therefore, the X-ray apparatus can be cheaply manufactured.

6) When the ratio of change of the second function when the tube voltage of the X-ray tube and/or the thickness of the object are set to variables is equal to or larger than predetermined values, the second function is corrected with respect to the tube voltage of the X-ray tube and/or the thickness of the object.

That is, when the second function has dependency on the tube voltage of the X-ray tube and/or the thickness of the object, the second function is corrected with respect to the tube voltage of the X-ray tube and/or the thickness of the object, thereby enabling dependency on the tube voltage and the thickness of the object of the second, fourth, or third function to be reflected in the calculation result (radiographic conditions), the radiographic conditions of the object can be more accurately determined.

7) In the X-ray apparatus, since means for calculating averaged object thickness first calculates the thickness of the object on the basis of the output level of the X-ray detection means at the time of the fluoroscopic exposure and the fluoroscopic conditions and determines the radiographic conditions on the basis of the thickness of the object, the radiographic conditions can be more properly determined.

8) Since the means for calculating averaged object thickness approximately calculates the thickness of the object on the basis of only the fluoroscopic conditions, for example, even if the intensity of the X-rays entering the X-ray detection means at the time of the fluoroscopic exposure exceeds a limit in which the intensity of X-ray can be properly detected, the thickness of the object can be almost accurately calculated.

Consequently, for example, even in a case where halation occurs in a fluoroscopic image, the thickness of the object can be almost accurately calculated. Thus, the X-ray radiographic conditions can be accurately determined.

9) Since an output level corrector increases the mAs value of the X-ray tube or the gain of the X-ray detection means at the time of the radiographic exposure by predetermined times on the basis of monitoring result of a tube saturation monitor, for example, even in the case where the gain of the X-ray detection means at the time of the fluoroscopic exposure cannot be raised to a proper level due to the thickness of the object, the X-ray radiographic conditions can be accurately calculated.

10) Since the predetermined values set for the X-ray exposing area and the distances from the object to the input face of the X-ray detection means are set to values which are most frequently used at the time of the fluoroscopic or radiographic exposure, an error occurring due to an approximation error or omission of the second function when the X-ray radiographic conditions are determined can be reduced.

Effects obtained by the representative techniques of the invention will be briefly described as follows.

1) When the X-ray radiographic conditions are determined from the X-ray fluoroscopic conditions, the radiographic conditions that make the output level of X-ray radiographic images proper can be determined in short time.

2) When the X-ray radiographic conditions are determined from the X-ray fluoroscopic conditions, the radiographic conditions in which the influence by the scattered X-ray can be determined.

3) Since the X-ray apparatus can be produced with a simple construction, the manufacturing costs of the X-ray apparatus can be reduced.

With respect to the second object of the invention, outlines of representatives techniques among techniques disclosed in the application and drawings will be briefly described as follows.

In the following description, imaging means denotes means for forming an X-ray transmission image.

(1) An X-ray apparatus for acquiring an X-ray image of an object by radiating X-rays to the object, comprises: X-ray radiation means for radiating X-rays to an object; imaging means for acquiring an X-ray image of the object; and radiation dose control means for controlling radiation dose so that the X-ray image having a predetermined X-ray relative noise level can be obtained on the basis of image level of a predetermined area in the X-ray image.

(2) An X-ray apparatus for acquiring an X-ray image of an object by radiating X-rays to the object, comprises: X-ray radiation means for radiating X-rays to the object; imaging means for acquiring an X-ray image of an object; radiation dose control means for controlling radiation dose so that the X-ray image having a predetermined X-ray relative noise level can be obtained on the basis of image level of a predetermined area in the X-ray image; and signal control means for controlling radiation dose and/or a signal amplification factor on the basis of image level of a predetermined area in the X-ray image so that an analog signal before being digitized in the imaging means is equal to or lower than a predetermined value.

(3) The X-ray apparatus described in (2), wherein the signal control means sets the X-ray relative noise level on the basis of maximum image level of the predetermined area in the X-ray image.

(4) The X-ray apparatus described in either one of (1) to (3), wherein the radiation dose control means sets the X-ray relative noise level on the basis of minimum image level of the predetermined area in the X-ray image.

(5) The X-ray apparatus described in either one of (1) to (4), wherein the X-ray image is one or more X-ray images which are acquired just before.

(6) The X-ray apparatus described in either one of (3) to (5) further comprises X-ray image prediction means for forming a predicted X-ray image to be acquired next by using linear lines or two- or larger-dimensional curves on the basis of the X-ray image. The radiation dose control means calculates a ratio of a first transformed level which transformed the minimum image level of the predetermined area in the predicted X-ray image into a preset standard condition to a second transformed level which transformed the minimum image level of the predetermined area in the X-ray image into the standard condition, and calculates the radiation dose from the product of the ratio and the X-ray dose in the standard conditions.

(7) The X-ray apparatus described in either one of (3) to (5), wherein the radiation dose control means performs a feedback control for calculating the ratio of the second transformed level to the standard level and calculating the radiation dose from the product of the ratio and the X-ray dose in the standard conditions.

(8) The X-ray apparatus described in (1) or (2), wherein the X-ray relative noise level is set on the basis of preliminarily acquired X-ray images of the object.

(9) The X-ray apparatus described in (1) or (2), wherein the X-ray relative noise level is set on the basis of information of the object obtained by measurement except for the X-ray radiographic exposure and the radiation dose of X-ray radiographic exposure which was performed in the past.

(10) The X-ray apparatus described in either one of (1) to (9) further comprises permissible range store means for storing the radiation dose value and an incident radiation dose or an amplification factor which are within a permissible range of the X-ray apparatus and the radiation dose value and the incident radiation dose or the amplification factor which exceed the permissible range. When the calculated radiation dose value and the incident dose or the amplification factor exceed the permissible range, the radiation dose control means and the output level control means use the values stored in the permissible range store means as calculation values.

(11) The X-ray apparatus described in either one of (1) to (10), wherein the radiation dose control means controls a pulse width of the X-ray tube in the X-ray radiation means.

(12) The X-ray apparatus described in either one of (1) to (10), wherein the radiation control means controls a voltage value of the X-ray tube in the X-ray radiation means.

(13) The X-ray apparatus described in either one of (1) to (12) further comprising: rotation means for rotating the X-ray radiation means and the imaging means around the object; and reconstruction means for reconstructing slice images of the object from the X-ray images.

(14) The X-ray apparatus described in either one of (2) to (13), wherein the signal control means is an optical iris or an amplification gain.

According to the means of (1), (4) to (6), and (10), the radiation dose control means calculates the ratio of the first transformed level which transformed the minimum image level of the predetermined area in the predicted X-ray image to the preset standard condition to the second transformed level which transformed the minimum image level of the predetermined area in one or more X-ray images acquired just before to the standard condition on the basis of the image level of the predetermined area in the predicted X-ray image to be acquired next which is formed by X-ray image predict means, and calculates the radiation dose from the product of the ratio and the X-ray dose in the standard conditions, and the X-ray radiation means radiates X-rays of the radiation dose to the object. Thus, the X-ray dose can be distributed so as to increase the S/N ratio of the three-dimensional image of the aimed area of the object for the same X-ray dose sum. Consequently, the dose of X-rays to be irradiated to the object can be reduced and the contrast resolution of the acquired X-ray image can be improved.

When the calculated radiation dose exceeds the limit radiation dose of the X-ray apparatus, the radiation dose control means uses a value stored in the limit store means as a radiation dose. Even if the calculated radiation dose is out of the limit in the X-ray apparatus, the reduction of the contrast resolution of the X-ray image can be therefore minimized.

The feedback control in which the radiation dose control means calculates the ratio of the first transformed level to the standard level and calculates the radiation dose from the product of the ratio and the X-ray dose in the standard conditions can also obtain almost the same effects as those mentioned above.

The details of the effects will be mentioned hereinlater.

According to the means of (2) to (6), and (10), the radiation dose control means calculates the ratio of the first transformed level which transformed the minimum image level of the predetermined area in the predicted X-ray image to the preset standard condition to the second transformed level which transformed the minimum image level of the predetermined area in one or more X-ray images acquired just before to the standard condition on the basis of the image level of the predetermined area in the predicted X-ray image to be acquired next which is formed by X-ray image predict means, and calculates the radiation dose from the product of the ratio and the X-ray dose in the standard conditions, and the X-ray radiation means radiates X-rays of the radiation dose to the object. Thus, the X-ray dose can be distributed so as to increase the S/N ratio of the three-dimensional image of the aimed area of the object for the same X-ray dose sum.

Further, since the output level control means controls incident dose and/or the signal amplification factor so that the analog signal before being digitized in the imaging means is equal to or lower than a predetermined level on the basis of the maximum image level of the predetermined area in the X-ray image, the limited dynamic range of the detector can be maximally used in the radiographic exposure at each angle.

Therefore, both of the settings of the X-ray dose and the image level can be compatibly performed.

The feedback control in which the radiation dose control means calculates the ratio of the first transformed level to the standard level and calculates the radiation dose from the product of the ratio and the X-ray dose in the standard conditions can also obtain almost the same effects as those mentioned above.

According to the means of (11), since the change in radiation dose is controlled by the pulse width of the pulse voltage applied to the X-ray radiation means, the deterioration of the contrast resolution in association with the change in X-ray energy spectrum can be prevented.

According to the means of (13), in addition to the above effects, the contrast resolution of the acquired X-ray image can be improved, so that the three-dimensional reconstructed image having high contrast resolution can be acquired.

According to the means of (14), the analog signal before being digitized in the imaging means can be easily controlled and the dynamic range of the detector can be maximally used.

Effects obtained by the representative techniques of the invention regarding the second object will be briefly described as follows.

(1) The X-ray dose can be distributed so that the S/N ratio of the three-dimensional image of the aimed area of the object increases for the same X-ray dose sum.

(2) The dose of X-rays to be radiated to the object can be reduced.

(3) In the measurement system having the two-dimensional X-ray detector whose dynamic range is limited, the X-ray dose setting and the image level setting for maximally using the limited dynamic range of the detector in the radiographic exposures at each angle can be performed compatibly.

(4) The contrast resolution of the X-ray image can be improved.

The foregoing and other objects and novel features of the invention will become apparent from the following description and the accompanying drawings.

BRIEF DESCRIPTION OF THE DRAWINGS

FIGS. 4A–4D are diagrams for explaining the relation of object thickness, a tube voltage, and averaged output signal intensity of an output image;

DETAILED DESCRIPTION OF THE PREFERRED EMBODIMENTS

Figure 1:
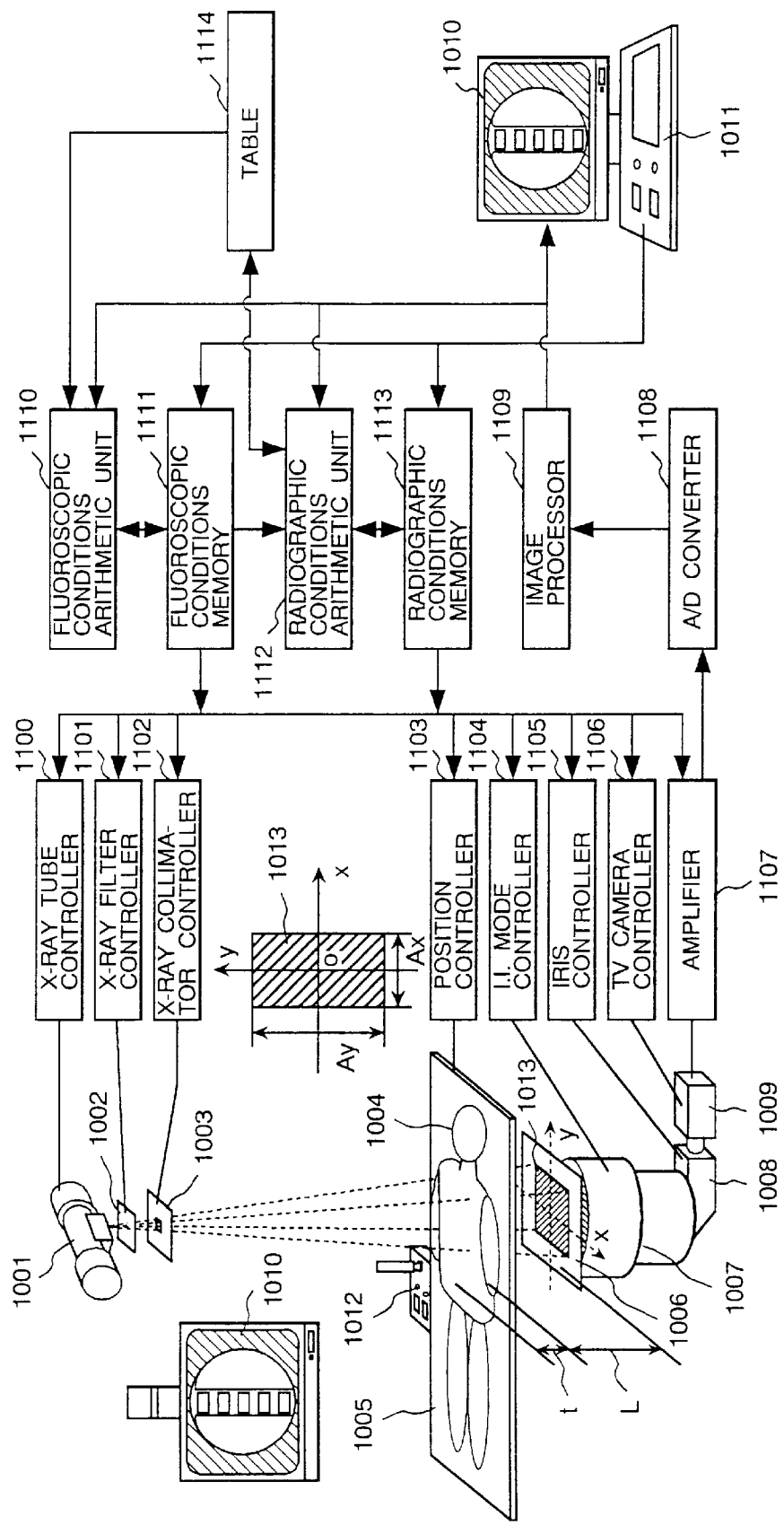
FIG. 1 is a block diagram showing a schematic construction of an X-ray apparatus according to an embodiment of the invention.

Embodiments of the invention will be described in detail hereinbelow with reference to the drawings.

In all of the drawings for explaining embodiments of the invention, the same reference numerals are designated to components having the same function and repetitive descriptions are omitted.

FIG. 1 is a block diagram illustrating a schematic construction of an X-ray apparatus according to the first embodiment of the invention.

In FIG. 1, an X-ray detector comprises an X-ray I. I. 1007, an optical lens system 1008, and a television camera 1009. An X-ray detecting system (X-ray detection means) is constructed by the X-ray detector and an amplifier 1107. Therefore, a gain and an output level of the X-ray detecting system are a gain and an output level of the amplifier 1107. An imaging system comprises an X-ray tube 1001, an X-ray filter 1002, an X-ray collimator 1003, an X-ray grid 1006, and the X-ray detector. A control system (control means) comprises controllers 1100 to 1106, the amplifier 1107, and a radiographic conditions memory 1113 for storing and outputting control information of the controllers. An object 1004 lies on a patient board 1005 of the bed and can variably change body position for radiography. An operator (not shown) sets a region of the object 1004 which is desired to be radiographed to the center part of the field of vision of the X-ray detector.

The distance between the X-ray tube 1001 and the input face of the X-ray I. I. 1007 is 120 cm, the thickness of the object 1004 is t, and the distance (hereinbelow, called an air gap) between the top face of the patient board 1005 of the bed and the input face of the X-ray I. I. 1007 is L.

t varies according to the individual difference or the body position of the object 1004. The air gap L changes according to the setting of the position of the patient board 1005 of the bed. The diameter of the X-ray input face of the X-ray I. I. 1007 is 30.48 cm. An (x, y) coordinate system is defined on the input face of the X-ray I. I. 1007. The origin of the coordinate system is in the center of the X-ray I. I. 1007, and an axial direction of the body is determined as a y axis and a direction which perpendicularly crosses the y axis is determined as an x axis. The X-ray grid 1006 is fixed on the input face of the X-ray I. I. 1007. In the television camera 1009, a high resolution charge-coupled device (CCD) is used as an imaging device.

Outline of each of the above elements will be described with reference to FIG. 1. The X-ray tube controller 1100 reads out a tube voltage (hereinbelow, described as a fluoroscopic tube voltage) and a tube current quantity (hereinbelow, described as a fluoroscopic mAs value) of the X-ray tube 1001 at the time of X-ray fluoroscopic exposure from a fluoroscopic conditions memory 1111 and controls generation of X-rays of the X-ray tube 1001 in a real time manner. The X-ray tube controller 1100 also reads out a tube voltage (hereinbelow, described as a radiography tube voltage), a tube current quantity (hereinbelow, described as a radiographic mAs value), and exposing time of the X-ray tube 1001 at the time of X-ray radiographic exposure from the radiographic conditions memory 1113 and controls X-ray generation of the X-ray tube 1001 on the basis of the read values.

The X-ray filter controller 1101 reads the kind and the presence or absence of the X-ray filter 1002 at the time of the X-ray fluoroscopic and radiographic exposure from the fluoroscopic conditions memory 1111 and the radiographic conditions memory 1113, respectively, and controls the kind and the presence or absence of the X-ray filter 1002 on the basis of the read values. The X-ray filter 1002 is used to change the energy spectrum of the X-rays radiated from the X-ray tube 1001.

The x-ray collimator controller 1102 reads the position of the X-ray collimator 1003 for setting an X-ray exposing area 1013 at the time of the X-ray fluoroscopic and radiographic exposures from the fluoroscopic conditions memory 1111 and the radiographic conditions memory 1113 and controls the position of the X-ray collimator 1003 on the basis of the read value. The X-ray exposing area 1013 is defined as an exposing area of X-rays on the input face of the X-ray I. I 1007. The X-ray collimator 1003 can change the X-ray exposing area 1013 in both of the x and y axis directions. The amount of change is symmetrical with respect to the x and y axes, respectively. The sizes of the X-ray exposing area in the x and y axis directions are expressed by Ax and Ay, respectively.

The position controller 1103 is a device for controlling an X-ray fluoroscopic and radiographic position of the object 1004. The fluoroscopic and radiographic position can be controlled either by moving the whole imaging system for the fixed patient board 1005 of the bed, by moving the patient board 1005 of the bed for the fixed imaging system, or by combination of the movements.

The I. I. mode controller 1104 reads I. I. modes of the X-ray I. I. 1007 at the time of the X-ray fluoroscopic and radiographic exposures from the fluoroscopic conditions memory 1111 and the radiographic conditions memory 1113 and controls the I. I. mode of the X-ray I. I. 1007. The I. I. mode specifies an X-ray detection area of the X-ray I. I. 1007. For example, 7, 9, and 12 inch modes are prepared as I. I. modes in the X-ray I. I. 1007. The X-rays are detected in the area of a circle having a diameter of 7, 9, or 12 inches (where, one inch is defined as 2.54 cm) on the input face of the X-ray I. I. 1007.

The iris controller 1105 reads an iris area of the optical lens system 1008 at the time of the X-ray fluoroscopic and radiographic exposures from the fluoroscopic conditions memory 1111 and the radiographic conditions memory 1113 and controls a known iris mechanism (not shown) on the basis of the read value.

The television camera controller 1106 reads a scanning condition of the television camera 1009 at the time of the X-ray fluoroscopic and radiographic exposures from the fluoroscopic conditions memory 1111 and the radiographic conditions memory 1113 and controls the scanning condition of the television camera 1009 on the basis of the read value. The television camera controller 1106 also controls a scan timing of the television camera 1009. Although a standard scan mode of the television camera 1009 at the time of the X-ray fluoroscopic exposure is 30 frames per second and the number of scanning lines of 1050 in the embodiment, fluoroscopic exposure in which the number of frames per second is 60 and the number of scanning lines is 525 can be also performed. Although a standard number of scanning lines of the television camera 1009 at the time of the X-ray radiographic exposure is 2100, radiographic exposure in which the number of scanning lines is 1050 or 525 can be also performed.

The amplifier 1107 reads a gain of an output signal of the television camera 1009 at the time of the X-ray fluoroscopic and radiographic exposures from the fluoroscopic conditions memory 1111 and the radiographic conditions memory 1113 and executes a control.

The X-ray exposing area 1013, the X-ray fluoroscopic and radiographic position, the kind of the X-ray grid 1006, the I. I. mode, and the scanning condition of the television camera 1009 at the time of fluoroscopic and radiographic exposures are manually set by the operator (not shown) through a remote operation console 1011 or an operation console 1012. The tube voltage and the tube current of the X-ray tube 1001, the kind of the X-ray filter 1002, the area of the optical iris, and the gain of the amplifier 1107 at the time of the fluoroscopic and radiographic exposures can be manually set by the operator (not shown) through the remote operation console 1011 or the operation console 1012 and also can be automatically set. The image acquisition time at the time of the radiographic exposure is automatically set by a method (procedure) which will be mentioned hereinlater. In addition to the above settings, a target region for imaging (for example, the chest, the abdomen, or the like) of the object 4 and a split mode for radiography or the like can be also set by the remote operation console 1011 or the operation console 1012. As split modes in this case, a non-split mode, an upper and lower 2-split mode, a right and left 2-split mode, a 4-split mode are prepared.

In the following description, a tube voltage V or a mAs value Q of the X-ray tube 1001 (where, the mAs value Q is defined as the product of the tube current of the X-ray tube 1001 and read time of one frame of the television camera 1009 at the time of the X-ray fluoroscopic exposure and is defined as the product of the tube current of the X-ray tube 1001 and exposing time at the time of the radiographic exposure), the kind of the X-ray filter 1002, Ax and Ay expressing the X-ray exposing area 1013, the air gap L, the kind of the X-ray grid 1006, I. I. mode, the area $\Omega$ of the iris, the scanning condition of the television camera 1009, and the state of the gain G of the amplifier 1107 are used as parameters. Setting values of the parameters at the time of the fluoroscopic and radiographic exposures are used as fluoroscopic conditions and radiographic conditions, respectively. The fluoroscopic conditions are stored into the fluoroscopic conditions memory 1111 and the radiographic conditions are stored into the radiographic conditions memory 1113.

The operation of the X-ray apparatus according to the embodiment will be described with reference to FIG. 1. At the time of the fluoroscopic and radiographic exposures, energy spectrum of X-rays generated by the X-ray tube 1001 is changed by the X-ray filter 1002, the X-ray exposing area 1013 is regulated by the X-ray collimator 1003, and after that, the X-rays are radiated to the object 1004.

A part of the X-rays radiated to the object is scattered by the object 1004 when the X-rays transmit the object 1004. Although the most part of the scattered X-rays is shielded by the X-ray grid 1006, a part is not shielded and is transmitted through the X-ray grid 1006. The scattered X-rays transmitted the X-ray grid 1006 and the primary X-rays which are not scattered but transmitted the object 1004 are simultaneously detected on the input face of the X-ray I. I. 1007 and are converted into an optical image. The quantity of light of the optical image derived by the conversion by the X-ray I. I. 1007 and projected from the output face is adjusted by a known optical iris (not shown) in the optical lens system 1008 and the optical image is formed on the television camera 1009. The television camera 1009 converts the optical image into video signals which are outputted to the amplifier 1107. The intensity of the video signal inputted to the amplifier 1107 is adjusted by the amplifier 1107 and the analog signal is converted into a digital signal by an AD converter 1108. The digital video signal is subjected to a predetermined imaging process by an image processor 1109 and the result is displayed on a display screen of a monitor 1010.

At the time of the fluoroscopic exposure, the video signal outputted from the image processor 1109 is supplied to a fluoroscopic conditions arithmetic unit 1110.

The fluoroscopic conditions arithmetic unit 1110 calculates, in a real time manner, the fluoroscopic tube voltage V, and the mAs value Q of the X-ray tube 1, the area $\Omega$ of the iris and the gain G of the amplifier 1107 by which the video signal output is changed to a preset level (proper level) and overwrites the values on respective storing locations in the fluoroscopic conditions memory 1111. The proper level of the video signal output at the time of the fluoroscopic exposure depends on the target region of the object and the split mode. The proper levels are preliminarily stored in a table 1114. The fluoroscopic conditions arithmetic unit 1110 sets the proper level for the video signal output at the time of the fluoroscopic exposure by referring to the table 1114 from the set values of the target region of the object and the split mode stored in the fluoroscopic conditions memory 1111 through the remote operation console 1011 or the operation console 1012 by the operator (not shown).

The fluoroscopic conditions arithmetic unit 1110 selects a proper X-ray filter from the set value of the target region of the object and the fluoroscopic tube voltage V stored in the fluoroscopic conditions memory 1111 and overwrites it on the fluoroscopic conditions memory 1111. As an example of a method of selecting the X-ray filter, for example, there is a method described in "electromedica 62", 1994, No. 1, p19–22, or the like.

The fluoroscopic conditions memory 1111 holds the fluoroscopic tube voltage V and the mAs value Q of the X-ray tube, the area $\Omega$ of the iris, and the gain G of the amplifier 1107 which are inputted from the fluoroscopic conditions arithmetic unit 1110 and also information such as the X-ray exposing area (Ax, Ay), the fluoroscopic and radiographic position, the kind of the X-ray grid, the I. I. mode, the value of the scanning condition of the television camera 1009, the setting value of the region of the object, the setting value of the split mode and the like which are inputted through the remote operation console 1011 or the operation console 1012 by the operator (not shown). The controllers control the apparatuses in real time according to the above information and the control result is reflected in the intensity of the video signal and is fed back to the fluoroscopic conditions arithmetic unit 1110.

At the time of the fluoroscopic exposure, the operator (not shown) performs a positioning by using the remote operation console 1011 or the operation console 1012 so that the target region of the object 1004 is positioned to a proper position on the display screen of the monitor 1010, allows a signal indicative of start of radiographic exposure to be generated by using the remote operation console 1011 or the operation console 1012 when the target region of the object 1004 is properly positioned, and executes the radiographic exposure.

When the signal indicative of start of radiographic exposure is generated, the X-ray tube controller 1100 stops the generation of X-rays and finishes the fluoroscopic exposure. Simultaneously, a radiographic conditions arithmetic unit 1112 reads the fluoroscopy conditions at the end of the fluoroscopic exposure from the fluoroscopic conditions memory 1111 and also reads the information such as an X-ray exposing area (A'x, A'y) at the time of the radiographic exposure (which is discriminated from the setting values of the fluoroscopic conditions by adding prime (') to the setting values of the radiographic conditions in the following description), the I. I. mode, and the scanning condition of the television camera 1009 at the time of the radiographic exposure from the radiographic conditions memory 1113. Further, the radiographic conditions arithmetic unit 1112 calculates a tube voltage V', a mAs value Q', an area $\Omega'$ of the iris, and a gain G' of the amplifier 1107 at the time of the radiographic exposure with reference to the table 1114 by a method which will be mentioned later, and stores the calculation results into the radiographic conditions memory 1113. Simultaneously, the controllers reads the radiographic conditions from the radiographic conditions memory 1113 and executes settings according to the setting values. Upon completion of the settings, the X-ray tube controller 1100 sends an X-ray generation signal to the X-ray tube 1001 and the radiographic exposure is performed. An X-ray image acquired by the radiographic exposure is converted to digital signals by the AD converter 1108 and the digital signals are stored into a frame memory (not shown).

Figure 2:
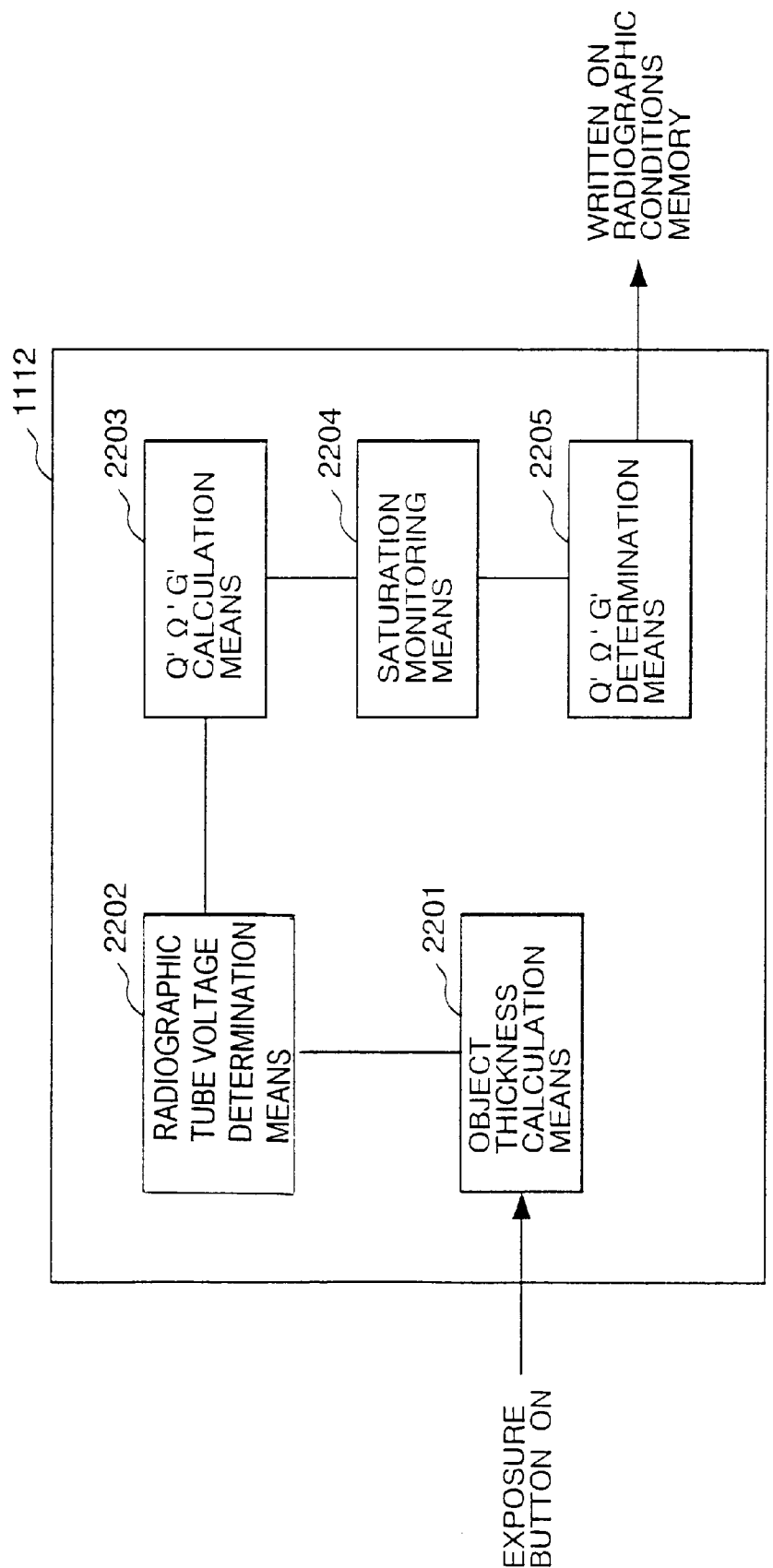
FIG. 2 is a block diagram showing a schematic construction of a radiographic conditions arithmetic unit of the embodiment.

FIG. 2 is a block memory showing a schematic construction of the radiographic conditions arithmetic unit of the embodiment. The radiographic conditions arithmetic unit 1112 comprises an object thickness calculation means (averaged object thickness calculation means) 2201, a radiographic tube voltage determination means 2202, a Q',$\Omega'$,G' calculation means 2203, a saturation monitoring means (tube saturation monitor, output level corrector) 2204, and a Q',$\Omega'$,G' determination means 2205.

In the embodiment, the respective means shown in FIG. 2 are realized by a program executed on a known information processing apparatus.

In FIG. 2, the object thickness calculation means 2201 calculates the thickness of the object 1004 from the relation between the object thickness at the time of the fluoroscopic exposure and the video signal output from the amplifier 1107. The details of the means 2201 will be described hereinlater.

The radiographic tube voltage determination means 2202 determines so called a radiographic tube voltage applied to the X-ray tube 1001 at the time of the radiographic exposure. In the embodiment, the radiographic tube voltage is determined by referring to the relevant radiographic tube voltage in a table 3114b on the basis of the object thickness t determined by the object thickness determination means 2201 and the target imaging region. The details will be described hereinlater.

The Q',Ω',G' calculation means 2203 calculates the mAs value Q', the area Ω' of the iris, and the gain G' of the amplifier 1107 so that an averaged output signal intensity of an output image based on the radiographic conditions inputted by the not-shown operator using the remote operation console 1011 or the operation console 1012 and an averaged output signal intensity of the output image at the time of the fluoroscopic exposure become equal. The details will be described hereinlater.

The saturation monitoring means 2204 determines whether each of the tube voltage V, the mAs value Q, the area Ω of the iris, and the gain G of the amplifier 1107 at the time of the fluoroscopic exposure is set to a permissible maximum level or not, that is, whether the fluoroscopic conditions are saturated or not, and executes the following processes on the basis of the result.

When the levels are not set to the permissible maximum levels, the tube voltage V', the mAs value Q', the area Ω' of the iris, and the gain G' of the amplifier 1107 determined by the radiographic tube voltage determination means 2202 and the Q',Ω',G' calculation means 2203 are used as levels for the radiographic exposure.

On the other hand, when the levels are set to the permissible maximum levels, the product of the mAs value Q', the area Ω' of the iris, and the gain G' of the amplifier 1107 determined by the Q',Ω',G' calculation means 2203 is multiplied by (proper level of the signal output at the time of the radiographic exposure)/(averaged output signal intensity of the output image based on the calculated values). The details will be described hereinlater.

The Q',Ω',G' determination means 2205 obtains Q', Ω', and G' from Q'Ω'G' obtained by the saturation monitoring means 2204 and after that, records them as setting values 3315 by an automatic exposure control for radiography into the radiographic conditions memory 1113.

Figure 3:
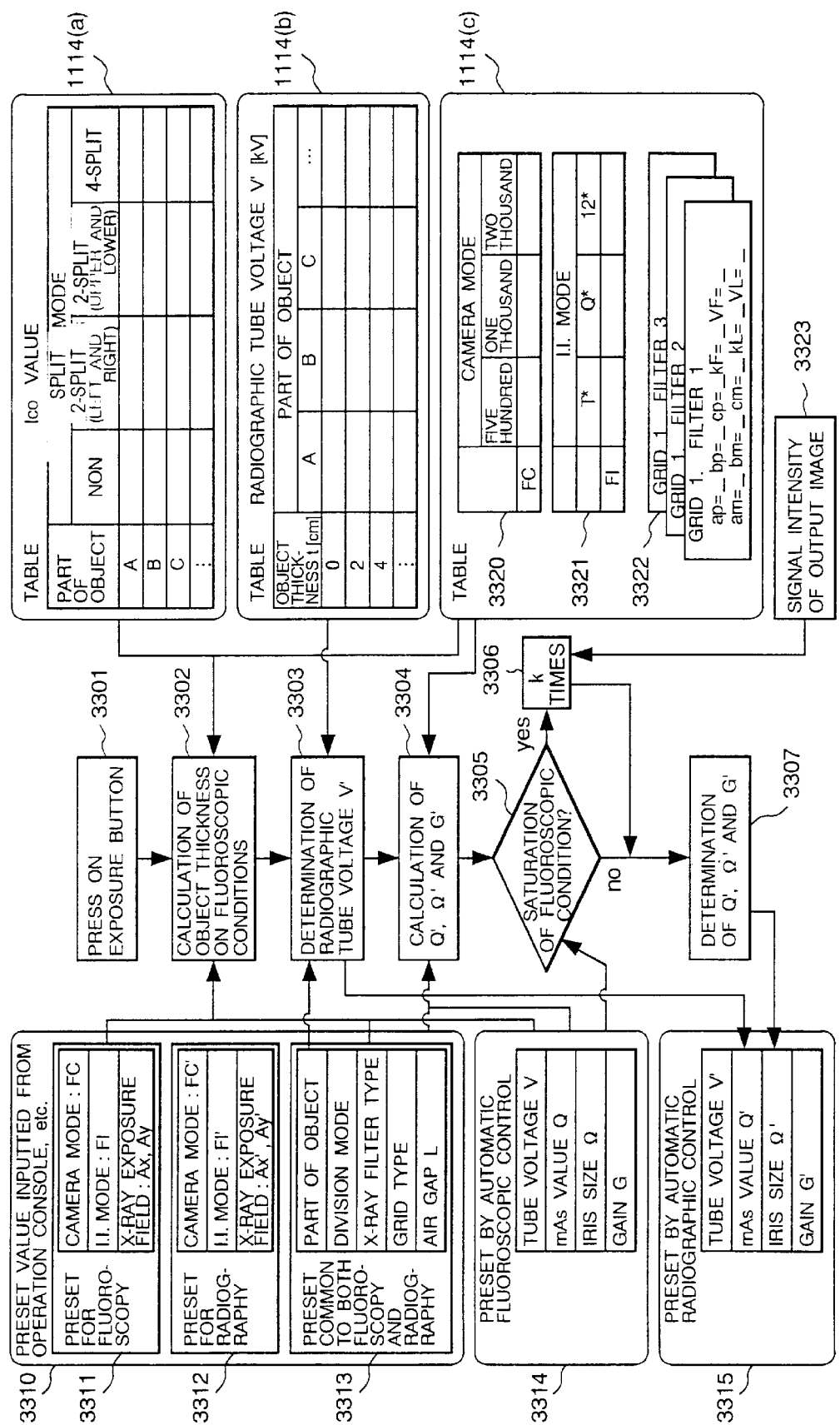
FIG. 3 shows a processing flow for explaining processes since generation of a signal indicative of start of X-ray radiographic exposure until determination of all of X-ray conditions.

FIG. 3 shows a processing flow for explaining processes from the generation of the signal indicative of the start of the radiographic exposure to determination of all of the radiographic conditions. Processes in the radiographic conditions arithmetic unit 1112 shown in FIG. 2 will be described hereinbelow with reference to FIG. 3.

The outline of the whole process will be described first. The processing flow is started by turning on an exposure button provided on the remote operation console 1011 or that on the operation console 1012 by the operator (not shown) (step 3301).

When "on" of the exposure button is detected, the object thickness calculation means 2201 in the radiographic conditions arithmetic unit 1112 reads all of the fluoroscopic conditions recorded in the fluoroscopic conditions memory 1111 upon completion of the fluoroscopic exposure, and calculates the average object thickness t in the X-ray exposing area of the object 1004 with referring to tables 1114a and 1114c (step 3302). Specifically, the above-mentioned fluoroscopic conditions are setting 3311 for fluoroscopic exposure and setting 3313 commonly used for the fluoroscopic and radiographic exposures in setting values 3310 inputted from the remote operation console 1011, the operation console 1012, or others, and setting values 3314 by the automatic exposure control for fluoroscopy.

The tube voltage determination means 2202 determines a proper radiographic tube voltage V' from the value of the average object thickness t and the setting value of the object's region with reference to a table 1114b and records the radiographic tube voltage V' in the radiographic conditions memory 1113 (specifically, the setting values 3315 by the automatic exposure control for radiography) (step 3303).

The Q',Ω',G' calculation means 2203 reads the object thickness t, the radiographic tube voltage V', and all of the fluoroscopic and radiographic conditions recorded in the fluoroscopic conditions memory 1111 and the radiographic conditions memory 1113 and calculates the product Q'Ω'G' of the mAs value Q', the area Ω' of the iris, and the gain G' upon radiographic exposure with reference to the table 1114c (step 3304). Specifically, the radiography conditions in this step are the setting values 3310 inputted from the remote operation console 1011, the operation console 1012, or others and the setting values 3314 by the automatic exposure control for fluoroscopy.

The saturation monitoring means 2204 determines whether the setting values 3314 by the automatic exposure control for fluoroscopy are set to values which maximize the signal intensity of the output image or not, that is, whether the fluoroscopic conditions are saturated or not (step 3305). If the fluoroscopic conditions are not saturated, it is determined that the Q'Ω'G' which is already determined is proper and the processing routine is advanced to next step 3307. On the other hand, when they are saturated, as will be described hereinlater, since the determined Q'Ω'G' is evaluated smaller than the proper value, the determined Q'Ω'G' is multiplied by (k) in order to correct the value to the proper value (step 3306). After that, the processing routine is advanced to next step 3307. The value of (k) is determined by a method, which will be described hereinlater, with the signal intensity 3323 of the output image acquired when the fluoroscopic exposure is finished.

Finally, the Q',Ω',G' determination means 2205 determines each of Q', Ω', and G' for the obtained Q'Ω'G' value and records the values as setting values 3315 by the automatic exposure control for radiography into the radiographic conditions memory 1113 (step 3307), thereby finishing the setting of the radiographic conditions by the radiographic conditions arithmetic unit 1112.

Processes by the respective means of the radiographic conditions arithmetic unit 1112 according to the embodiment will be concretely described with reference to FIGS. 2 and 3.

In the object thickness calculation means 2201, in order to calculate the average thickness t in the X-ray exposing area of the object 1004, an expression (1) (first function) relating the object thickness and the signal intensity of the output image under the fluoroscopic conditions is used.

$$I_c = Q \Omega G F C F I P_0(V) e^{-\mu(V) t} FF(V, t, A_x, A_y) FL(V, t, L) \qquad (1)$$

In the expression (1), an averaged output signal intensity Ic denotes the average of the output signal intensity in the center part of an image outputted from the AD converter 1108.

Although Ic is the average of the output signals in a ¼ center region (length of one side) in the output image (for example, the average of output signals in the center region of 525×525 pixels of an image which is scanned by the number of scanning lines of 2100 and is sampled by the AD converter), the invention is not limited to the above.

FC and FI denote coefficients determined by the scan mode of the television camera 1009 and I.I. mode, respectively. FC and FI are preliminarily measured with respect to all of the scan modes and the I.I. modes. Po(V) indicates an averaged output signal intensity function for air and shows averaged output signal intensity of detected X-rays which transmitted through air when the object 1004 does not exist. Generally, Po(V) changes depending on the tube voltage V and can be approximated by a quadratic function as shown by an expression (2).

$$P_o(V) = ap\ V^2 + bp\ V + cp \quad (2)$$

In the expression (2), ap, bp, and cp as coefficients of the quadratic function can be preliminarily measured. $\mu(V)$ is a function of an X-ray absorption coefficient of the object 1004. Generally, $\mu(V)$ changes depending on the tube voltage V and can be approximated by a quadratic function as shown by an expression (3).

$$\mu(V) = am\ V^2 + bm\ V + cm \quad (3)$$

In the expression (3), the values am, bm, and cm which are coefficients of the quadratic function are preliminarily measured with respect to materials such as an acrylic board, water, and the like stimulating the object 1004. FF(V, t, Ax, Ay) is a function of a rate of change of the averaged output signal intensity in response to the change in the X-ray exposing area. Generally, the change amount of FF(V, t, Ax, Ay) to the X-ray exposing area (Ax, Ay) depends on the tube voltage V and the object thickness t and can be approximated by the following expression (4) (third function).

$$FF(V, t, A_x, A_y) = 1 - KF(V-VF)t\{(A_o-A_x) + (A_o-A_y)\} \quad (4)$$

In the expression (4), a coefficient KF and a tube voltage VF characterizing FF(V, t, Ax, Ay) are preliminarily measured with respect to the materials such as acrylic board, water, and the like stimulating the object 1004. Ao is a value set as a standard size of the X-ray exposing area (Ax, Ay). In the expression (4), FF(V, t, Ax, Ay) is equal to 1 when the X-ray exposing area (Ax, Ay) is the standard size Ao. The expression (4), consequently, expresses the rate of change of the averaged output signal intensity in response to the change of the X-ray exposing area (Ax, Ay). FL(V, t, L) denotes a function of the rate of change of the averaged signal output in response to the change in air gap. Generally, the rate of change of FL(V, t, L) in response to the air gap L depends on the tube voltage V and the object thickness t and can be approximated by the following expression (5) (fourth function).

$$FL(V, t, L) = 1 - KL(V-VL)t(L-L_o) \quad (5)$$

In the expression (5), a coefficient KL and a tube voltage VL characterizing FF(V, t, L) are preliminarily measured with respect to the materials such as acrylic board, water, and the like stimulating the object 1004. Lo is a value set as a standard value of the air gap L. In the expression (5), FL(V, t, L) is equal to 1 when the air gap L is the standard value Lo. The expression (5), consequently, expresses the rate of change of the averaged output signal intensity in response to the change in air gap L. Among the parameters characterizing the expressions (1) to (5), FC and FI are preliminarily measured with respect to combinations of specific X-ray filters 1002 and the anti-scattering grids 1006 and are stored in the table 1114c. The values of ap, bp, cp, am, bm, cm, KF, VF, KL, and VL are preliminarily measured with respect to the combinations of all of the kinds of the X-ray filters 1002 and the grids 1006 and are stored in the table 1114c. Methods of deriving the expressions (1) to (5) and the measurement methods of the parameters stored in the table 1114c will be described hereinlater.

As mentioned above, the fluoroscopic conditions arithmetic unit 1110 executes a fluoroscopic control so that the averaged output signal intensity Ic is kept to be the proper value Ico. The proper values Ico are preliminarily measured with respect to the materials such as an acrylic board, water, and the like stimulating the object 1004. Ico is set as a value which varies according to the object's region or the split mode and the values Ico are stored in the table 1114a.

When the average thickness t of the object 1004 is calculated in the object thickness calculation means 2201, the fluoroscopic conditions stored in the fluoroscopic conditions memory 1111, that is, all of the settings 3311 for fluoroscopy and the settings 3313 commonly used for radiography and fluoroscopy in the setting values 3310 which are input through the remote operation console 1011, the operation console 1012, or others, and the setting values 3314 set by the automatic exposure control for fluoroscopy are read out. Subsequently, FC and FI are read out from the table 1114c for the camera mode and the I. I. mode in the fluoroscopic conditions. The parameters ap, bp, cp, am, bm, cm, KF, VF, KL, and VL are read out from the table 1114c for the setting values of the kind of the grid and the kind of the X-ray filter in the fluoroscopic conditions. Further, the setting value Ico of the averaged output signal intensity is read out from the table 1114a according to the setting values of the object region setting and the split mode setting in the fluoroscopic conditions. Since all of the parameter values except for the averaged object thickness t are read and determined in the right side of the expression (1), the averaged object thickness t which sets the averaged output signal intensity of the left side of the expression to Ico can be determined. Specifically, t satisfying the expression (1) can be calculated by using a numerical value calculating method such as the Newton's method or the bisection method. As another calculating method, the right side of the expression (1) is calculated as values of t at different numerical points, for instance, 5, 10, 15, 20 [cm] or the like, those values are subjected to the least square fitting method by an exponential function $a \times \exp(-bt)$ (where, a and b are variables determined by the fitting method), thereby enabling the object thickness t to be easily obtained by $t = (\log a - \log Ico)/b$.

There is another method of obtaining the averaged object thickness t, in which an actual averaged output signal intensity Ic is calculated from a fluoroscopic image when the fluoroscopic exposure is completed and is used as an averaged output signal intensity Ic of the left side of the expression (1). According to the method, since the arithmetic operation is executed by using the actually measured value of the averaged output signal intensity, a more accurate object thickness t can be obtained. When halation occurs in the center ¼ area (length of one side) of the fluoroscopic image after completion of the fluoroscopic exposure, an accurate Ic cannot be derived. Therefore, when the occurrence of the halation has to be discriminated. When it is determined that halation occurs, it is necessary to calculate the average object thickness t by using the above-mentioned method in which the averaged output signal intensity of the left side of the expression (1) is set to Ico.

In the radiographic tube voltage determination means 2202, the radiographic tube voltage V' is determined according to the object thickness t determined by the object thickness calculation means 2201. The proper radiographic tube voltage V' according to the object thickness t is preliminarily set in the table 1114b, in which contrast and noises of the radiographic image, preference of the examiner, and the like are considered. Since the setting differs according to the regions of the object (distribution of the X-ray attenuation coefficients differs according to the regions of the object), table values can be prepared for the respective regions to be imaged of the object.

In the Q',Ω',G' calculation means 2203, Q'Ω'G' is calculated so that the averaged output signal intensity of the output image after completion of the fluoroscopic exposure and the averaged output signal intensity of the radiographic image are equal to the same value Ic. Since the output signal intensity of the fluoroscopic image when the fluoroscopic exposure is finished is controlled to a proper value by the automatic exposure control for fluoroscopy, the radiographic exposure can be executed so that the signal output intensity of the radiographic image becomes a proper value. Such Q'Ω'G' can be obtained from the expression (1) by the following expression (6).

$$Q'\Omega'G' = Q\Omega G \frac{FCFIP_o(V)}{FCFI'P_o(V')}$$ (6)

$$e^{-|\mu(V)-\mu(V')|t} \frac{FF(V, t, A_x, A_y)FL(V, t, L)}{FF(V', t, A'_x, A'_y)FL(V', t, L)}$$

All of the parameters of the right side of the expression (6) can be determined by referring to the object thickness t, the radiographic tube voltage V', the setting values 3310 inputted by the operation console or others, and the setting values 3314 by the automatic exposure control for fluoroscopy and the table 1114c, so that the expression (6) can be calculated.

The calculations in the Q',Ω',G' calculation means 2203 are executed on assumption that the output signal intensity of the fluoroscopic image upon completion of the fluoroscopic exposure is controlled to the proper value by the automatic exposure control for fluoroscopy. However, when the object 1004 is thick, when a contrast medium is used, or the like, there is a case that the automatic exposure control for fluoroscopy cannot be properly executed. This is because the output signal intensity of the fluoroscopic image at the time of the fluoroscopic exposure does not reach the proper value although all of the tube voltage V, the mAs value Q, the area Ω of the iris, and the gain G are set to the permissible maximum values. In this case, since the averaged output signal intensity Ic of the fluoroscopic image is smaller than the proper value Ico, it is necessary to correct Q'Ω'G' at the time of the radiographic exposure by being multiplied by k (=Ico/Ic) so that the output signal intensity of the radiographic image is equal to the proper value Ico.

The saturation monitoring means 2204 reads the setting values 3314 set by the automatic exposure control for fluoroscopy and determines whether all of the tube voltage V, the mAs value Q, the iris area Ω, and the gain G are set to the permissible maximum values or not, that is, the fluoroscopic conditions are saturated or not. The maximum value of each of the tube voltage V and the mAs value Q is determined by heat capacity of the X-ray tube 1001. The maximum of the iris area Ω is determined by the diameter of a lens used in the optical system 1008. The maximum of the gain G of the amplifier 1107 is preset by limitation of the S/N ratio of the fluoroscopic output image. When the fluoroscopic conditions are not saturated, the automatic exposure control for fluoroscopy is properly performed, so that Q'Ω'G' calculated by the Q',Ω',G' calculation means 2203 can be used as it is. When the fluoroscopic conditions are saturated, the automatic exposure control for fluoroscopy is not properly executed. Q'Ω'G' is, therefore, multiplied by k (=Ico/Ic) so that the output signal intensity of the radiographic image is equal to the proper value Ico (step 3306). The value read from the table 1114a in step 3302 can be used as the proper value Ico of the output signal intensity.

In step 3307, Q',Ω', and G' are respectively determined for the determined Q'Ω'G'. All of the above-mentioned determinations are automatically or partially manually performed by the operator (not shown) in consideration of absorbed dose of the object 1004, the spatial resolution of the radiographic image, the S/N of the radiographic image, and the like. Generally, when the mAs value Q is increased, the absorbed dose of the object 1004 is increased. When the iris area Ω' is enlarged, the spatial resolution of the radiographic image deteriorates. Further, when the camera gain G' is increased, the S/N of the radiographic image deteriorates. In case of executing the radiographic exposure by attaching greater importance to the picture quality of the radiographic image, the iris area Ω' and the camera gain G' are reduced and the mAs value Q' is contrarily increased. In case of executing the exposure by attaching greater importance to the reduction of the absorbed dose of the object 1004, the area Ω' of the iris and the camera gain G' are increased and the mAs value Q' is contrarily reduced.

Figure 5A:
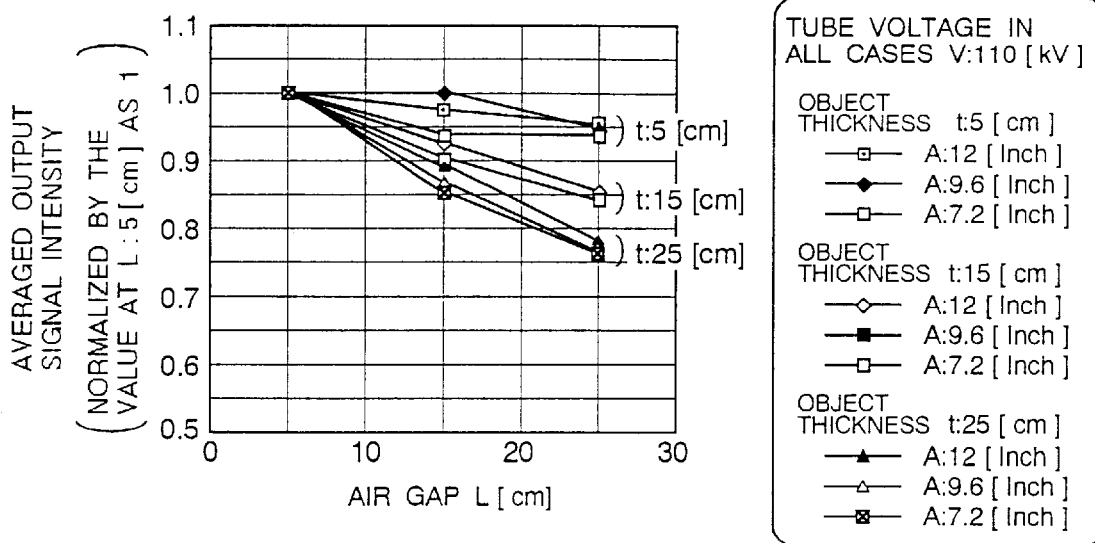
FIGS. 5A and 5B are diagrams for explaining the relation of change in air gap, change in X-ray exposing area, and averaged output signal intensity of an output image.
Figure 5B:
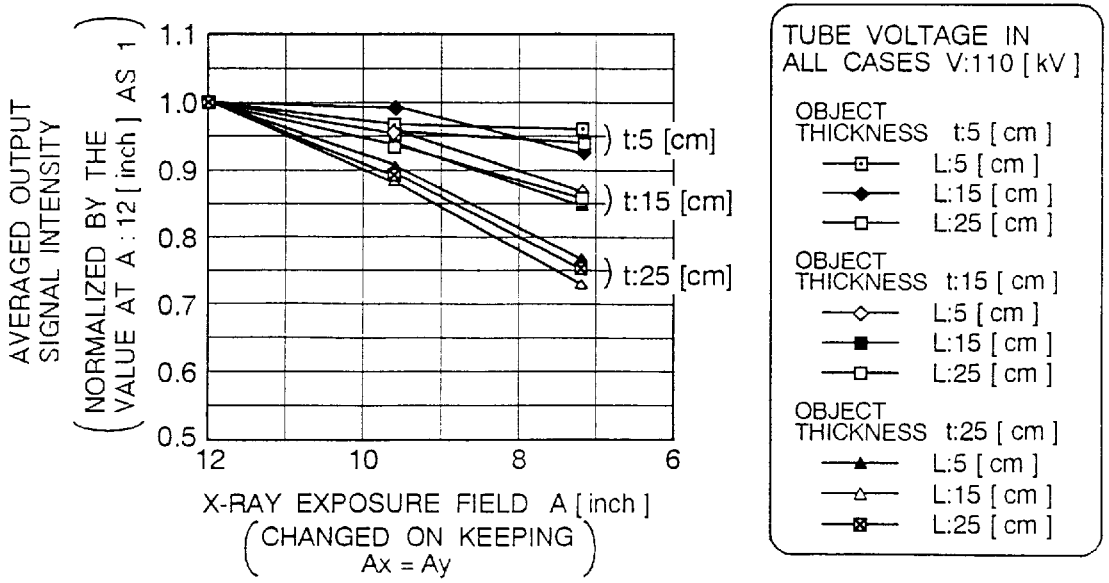
Figure 6A:
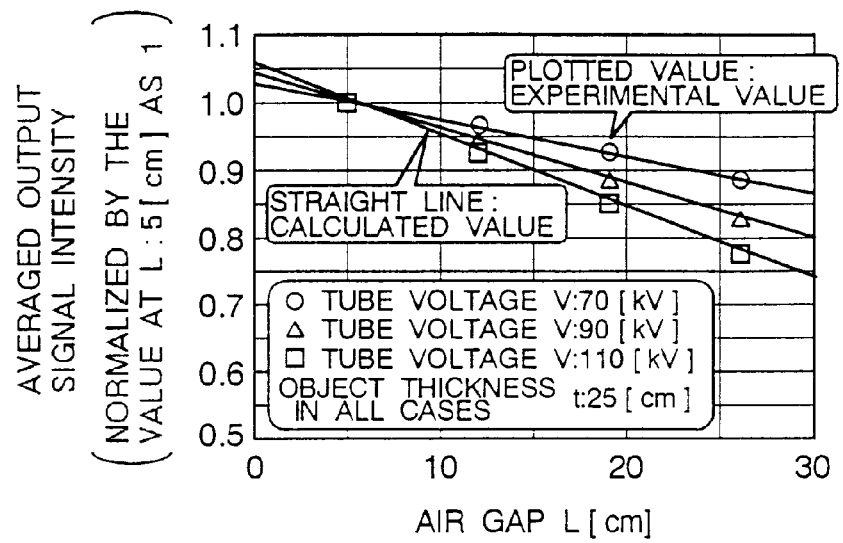
FIGS. 6A and 6B are diagrams for explaining the relation between the change in air gap and the averaged output signal intensity of the output image.
Figure 6B:
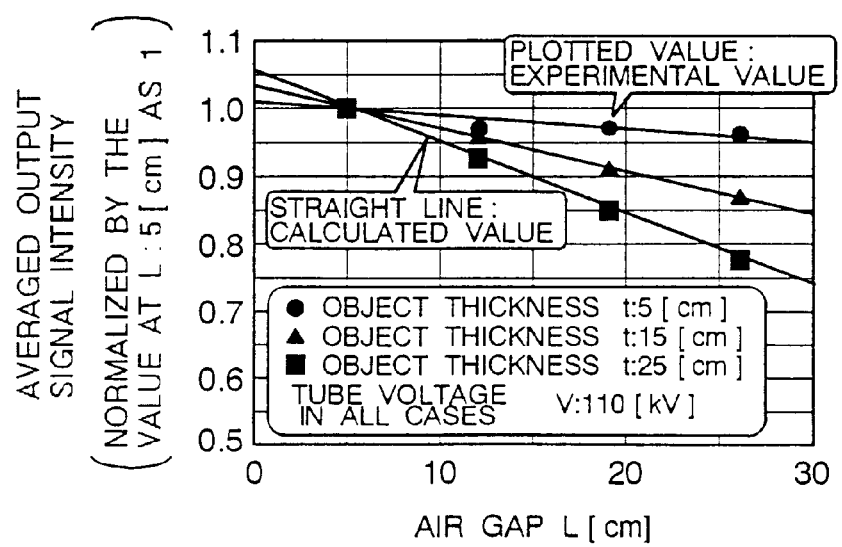
Figure 7A:
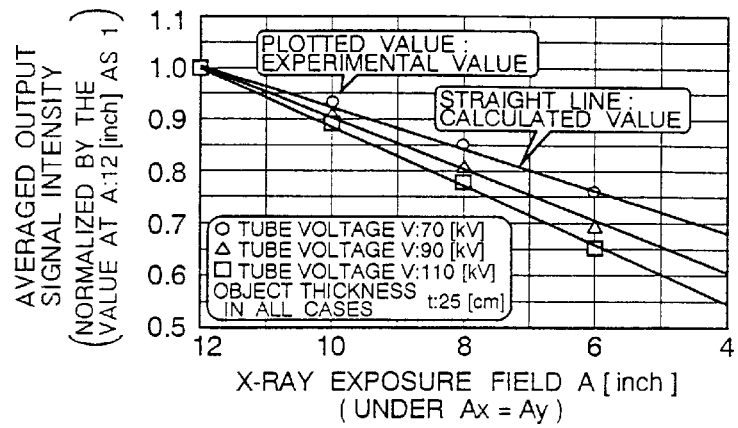
FIGS. 7A–7C are diagrams for explaining the relation between change in the X-ray exposing area and the averaged output signal intensity of the output image.
Figure 7B:
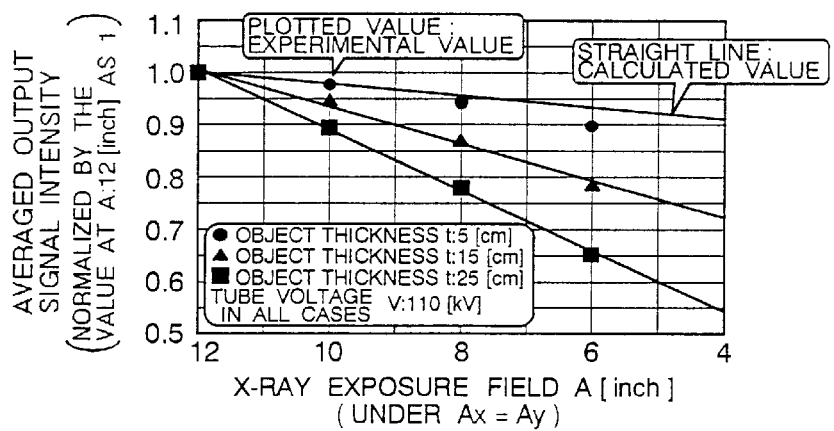
Figure 7C:
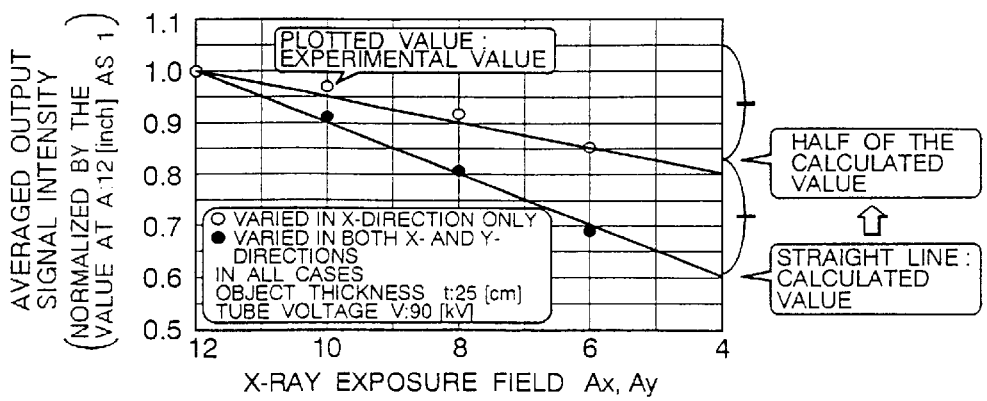

FIGS. 4A–4D are diagrams for explaining the relation of the object thickness and the tube voltage and the averaged output signal intensity of the output image. FIGS. 5A and 5B are diagrams for explaining the relation of the air gap L and the X-ray exposing area A and the averaged output signal intensity of the output image. FIGS. 6A and 6B are diagrams for explaining the relation between the air gap L and the averaged output signal intensity of the output image. FIGS. 7A–7C are diagrams for explaining the relation between the X-ray exposing area (Ax, Ay) and the averaged output signal intensity of the output image. Methods of deriving the expressions (1) to (5) relating the fluoroscopic conditions, the object thickness, and the signal intensity of the output image and methods of measuring the parameters ap, bp, cp, am, bm, cm, KF, VF, KL, and VL in the expressions (1) to (5) will be described.

First, in the expression (1) relating the fluoroscopic and radiographic conditions, the object thickness, and the signal intensity of the output image, especially, the relation of the object thickness t, the tube voltage V, and the averaged signal output intensity of the output image will be explained with reference to FIGS. 4A–4D. In the following description, standard levels are determined to all of the parameters except for the object thickness t and the tube voltage V, that is, the mAs value Q, the camera iris Ω, the gain G of the amplifier, the camera mode, the I. I. mode, the X-ray exposing area (Ax, Ay), and the air gap L. An example of the standard levels set to the parameters is, for instance, shown in FIG. 4(A). In measurement shown below, values shown in FIG. 4(A) are used as the standard levels. In the following description, a standard aluminum filter having the thickness of 0.5 mm is used as the kind of the X-ray filter 1002, a standard grid having a focal distance of 120 cm and the grid ratio of 1:12 is used as the kind of the X-ray grid, and a standard acrylic board is used as a material stimulating the object. Further, when Ax=Ay=A is kept, the X-ray exposing area (Ax, Ay) is expressed as an X-ray exposing area A for simplicity of explanation. In the following whole description regarding FIGS. 4A–4D, all of the parameters having the standard levels are fixed to the standard levels. In this case, each of FF(V, t, Ax, Ay) and FL(V, t, L) in the expression (1) is equal to 1 and Po(V) and $\mu$(V) characterizing the relation of the object thickness t and the tube voltage V and the signal intensity of the output image can be measured.

FIG. 4(B) is a diagram obtained by plotting measured values of the averaged output signal intensity Ic in the case where the object thickness t is changed every 5 cm from 5 to 25 cm when the tube voltage V=70, 85, 100, and 115 kV. FIG. 4(B) also shows the result of executing the least square fitting method to the plot values by an exponential function of Poxexp (–$\mu$t). The parameters Po and $\mu$ characterizing the exponential function are determined by the above-mentioned fitting method. Po and $\mu$ have tube voltage dependency and can be expressed as Po(V) and μ(V), respectively. The results of plotting the Po(V) and μ(V) determined with respect to the respective tube voltages V from FIG. 4(B) are shown in FIGS. 4(C) and 4 (D). FIGS. 4(C) and 4(D) also show the result of executing the least square fitting by the quadratic functions shown in the expressions (2) and (3). The parameters ap, bp, cp, and the parameters am, bm, and cm characterizing the expressions (2) and (3), respectively, are determined by the above-mentioned fitting method. Since the parameters have dependency on the tube voltage V of the X-ray tube 1, that is, the energy spectrum of the radiated X-ray, when the X-ray filter or the X-ray grid which changes the X-ray energy spectrum is changed, the parameters are generally changed. It is therefore necessary to preliminarily measure ap, bp, cp, am, bm, and cm for combinations of all of the kinds of the X-ray filters and grids to be used and to store the results in a table. With reference to FIGS. 4(B) to 4(D), it is understood that the fitting is almost properly executed by the fitting function which least squares the plot values. However, the fitting function is not limited to the example but can be replaced by a more proper one in accordance with a measurement value.

In the expression (1) relating the fluoroscopic and radiographic conditions and the object thickness and the signal intensity of the output image, especially, the relation of the change in the air gap L and the X-ray exposing area A and the averaged output signal intensity of the output image will be described with reference to FIGS. 5A and 5B.

FIG. 5(A) is a diagram showing a state of change in the averaged output signal intensity Ic when the air gap L is changed to 5, 15, and 25 cm while the tube voltage V is fixed to 110 kV. The averaged output signal intensity Ic is normalized by setting the averaged output signal intensity Ic to 1 when the air gap L is the standard level of 5 cm. FIG. 5(A), consequently, shows the rate of change of the averaged output signal intensity Ic. Generally, as obviously understood from FIG. 5(A), as the air gap L increases, the averaged output signal intensity decreases. This is because that as the air gap L increases, the dose of scattered X-rays entering the X-ray I. I. 1007 decreases. FIG. 5(A) also shows the results of examinations of the object thickness dependency and the X-ray exposing area dependency of the rate of change. According to FIG. 5(A), it is understood that the rate of change increases as the object thickness t is increased to 5, 10, and 15 cm. This is because that as the object thickness t increases, the ratio of the scattered X-rays to the primary X-rays is increased. It is also understood from FIG. 5(A) that even if the X-ray exposing area A is changed to 12, 9.6, and 7.2 square inches, the rate of change of the averaged output signal intensity is not so influenced.

FIG. 5(B) is a diagram showing a state of change in the averaged output signal intensity Ic when the X-ray exposing area A is changed to 12, 9.6, and 7.2 square inches while the tube voltage V is fixed to 110 kV. The averaged output signal intensity Ic is normalized by setting the averaged output signal intensity Ic when the X-ray exposing area A is at the standard level of 12 inches to 1.

As obviously understood from FIG. 5(B), as the X-ray exposing area A is reduced, the averaged output signal intensity decreases. This is because that as the X-ray exposing area A is reduced, X-rays are scattered in the peripheral part of the X-ray exposing area A and the dose of scattered X-rays entering the center part of the X-ray I. I. 1007 decreases. FIG. 5(B) also shows the results of examinations of the object thickness dependency and the air gap dependency of the rate of change. According to FIG. 5(B), it is understood that the rate of change increases as the object thickness t is increased to 5, 10, and 15 cm. This is because that as the object thickness t increases, the ratio of the scattered X-rays to the primary X-rays is increased. It is also understood from FIG. 5(B) that even if the air gap L is changed to 5, 15, and 25 cm, the rate of change of the averaged output signal intensity is not so influenced.

It can be concluded from FIGS. 5(A) and 5 (B) that the change in the averaged output signal intensity Ic can be regard almost independent from the changes in the air gap L and the X-ray exposing area A.

In the expression (1), therefore, the function FF(V, t, Ax, Ay) of the rate of change in the averaged output signal intensity for the change in the X-ray exposing area and the function FL(V, t, L) of the rate of change in the averaged output signal intensity for the change in the air gap are separated as independent functions.

In the expression (1) relating the fluoroscopic and radiographic conditions and the object thickness and the signal intensity of the output image, especially the relation between the change in the air gap L and the averaged output signal intensity of the output image will be described with reference to FIGS. 6A and 6B. In FIGS. 6A and 6B, especially, the rate of change of the averaged output signal intensity Ic is shown as a signal intensity of the output image. Since the expressing method is substantially the same as that of FIG. 5(A), the description is omitted here.

FIG. 6(A) shows the tube voltage dependency of the rate of change of the averaged output signal intensity Ic. FIG. 6(B) shows the object thickness dependency of the rate of change of the averaged output signal intensity Ic. As obviously understood from FIGS. 6(A) and 6(B), the rate of change of the averaged output signal intensity Ic has dependency on the tube voltage and the object thickness. This is because that as the object thickness and the tube voltage change, the ratio of the scattered X-rays to the primary X-rays is changed. In FIG. 6(A), the object thickness t is fixed to 25 cm, the air gap L is changed to 5, 12, 19, and 26 cm with respect to the cases where the tube voltage V is 70, 90, and 110 kV. Plot values in the diagram show experimental values. As obviously understood from the plot values, the averaged output signal intensity Ic almost linearly changes in response to the change in the air gap L, and the averaged output signal intensity Ic also changes almost linearly to the tube voltage V.

In FIG. 6(B), the tube voltage V is fixed to 110 kV, the air gap L is changed to 5, 12, 19, and 26 cm with respect to the cases where the object thickness t is 5, 15, and 25 cm. Plot values in the diagram show experimental values. As obviously understood from the plot values, the averaged output signal intensity Ic almost linearly changes in response to the change in the air gap L, and the averaged output signal intensity Ic changes almost linearly to the object thickness t.

Consequently, the function FL(V, t, L) of the rate of change of the averaged output signal intensity Ic in response to the change in the air gap L is approximated by the expression (5). VL characterizing the expression (5) is obtained by measuring values at two plot points in FIG. 6(A) (t=25 cm, L=26 cm, V =70, 110 kV) and by calculating VL which realizes FL(V, t=25 cm, L=26 cm)=1 from the measurement values and the expression (5). KL characterizing the expression (5) is easily calculated by using the expression (5) from the measurement value at (t=25 cm, L=26 cm, V=110 kV) among the above-mentioned measurement values and already derived VL. Since the parameters have dependency on the tube voltage V of the X-ray tube 1001, that is, the energy spectrum of the radiated X-ray, generally, when the X-ray filter or the X-ray grid which changes the X-ray energy spectrum is changed, the parameters are changed. It is therefore necessary to preliminarily measure VL and KL with respect to combinations of all of the kinds of the X-ray filters and grids to be used and to store the results in a table. In FIGS. 6(A) and 6(B), the averaged output signal intensity Ic calculated by using the expression (5) for KL and VL derived by the above-mentioned methods is also shown. According to FIGS. 6(A) and 6(B), it is understood that the change in the averaged output signal intensity Ic in response to the change in the air gap L is almost approximated by using the expression (5). Although it is approximated by the linear function in the expression (5) on assumption that the change in the averaged output signal intensity Ic with respect to the air gap L, the object thickness t, and the tube voltage V is linear, the approximation function is not limited to the example but may be replaced by a more proper one in accordance with a measurement value.

In the expression (1) relating the fluoroscopic and radiographic conditions and the object thickness and the signal intensity of the output image, especially the relation between the change in the X-ray exposing area (Ax, Ay) and the averaged signal intensity of the output image will be described with reference to FIGS. 7A–7C. FIGS. 7A–7C are diagrams showing the rate of change of the averaged output signal intensity Ic. Since the expressing method is basically the same as that of FIG. 4(B), the description is omitted here.

FIG. 7(A) shows the tube voltage dependency of the rate of change of the averaged output signal intensity Ic. FIG. 7(B) shows the object thickness dependency of the rate of change of the averaged output signal intensity Ic. As obviously understood from FIGS. 7(A) and 7(B), the rate of change of the averaged output signal intensity Ic has dependency on the tube voltage and the object thickness. This is because that as the object thickness and the tube voltage change, the ratio of the scattered X-rays to the primary X-rays is changed.

In FIG. 7(A), the object thickness t is fixed to 25 cm, and the X-ray exposing area A is changed to 12, 10, 8, and 6 inches with respect to the cases where the tube voltage V is 70, 90, and 110 kV. Plot values in the diagram show experimental values. As obviously understood from the plot values, the averaged output signal intensity Ic almost linearly changes in response to the change in the X-ray exposing area A, and the averaged output signal intensity Ic also changes almost linearly to the tube voltage V.

In FIG. 7(B), the tube voltage V is fixed to 110 kV, and the X-ray exposing area A is changed to 12, 10, 8, and 6 inches for each of the cases where the object thickness t is 5, 15, and 25 cm. Plot values in the diagram show experimental values. As obviously understood from the plot values, the averaged output signal intensity Ic almost linearly changes in response to the change in the X-ray exposing area A, and the averaged output signal intensity Ic also changes almost linearly to the object thickness t.

FIG. 7(C) shows the change in the averaged output signal intensity Ic with respect to both of a case where the X-ray exposing area is changed in both of the x and y directions and a case where the X-ray exposing area is changed only in the x direction (in this case, the y direction is fixed to the standard level of 12 inches). In FIG. 7(C), the object thickness t is fixed to 25 cm, the tube voltage is fixed to the 90 kV, and the X-ray exposing area (Ax, Ay) and Ax are changed to 12, 10, 8, and 6 inches respectively. Plot values in the diagram show experimental values. As obviously understood from the plot values that the change amount of the averaged output signal intensity Ic when the X-ray exposing area is changed only in the x direction is almost the half of the change amount of the averaged output signal intensity Ic when the X-ray exposing area is changed in both of the x and y directions. It can be therefore concluded that the averaged output signal intensity Ic changes in proportional to the sum of the change amount in Ax and the change amount in Ay.

Consequently, the function FL(V, t, Ax, Ay) of the rate of change of the averaged output signal intensity Ic in response to the change in the X-ray exposing area (Ax, Ay) is approximated by the expression (4). VF characterizing the expression (4) is obtained by measuring values at two plot points in FIG. 7(A) (t=25 cm, A=6 inches, V=70, 110 kV) and by calculating VF realizing FF(V, t=25 cm, Ax=6 inches, Ay=6 inches)=1 from the measurement values and the expression (4). KF characterizing the expression (4) is easily calculated by using the expression (4) from the measurement value at (t=25 cm, A=6 inches, V=110 kV) and already derived VF. Since the parameters have dependency on the tube voltage V of the X-ray tube 1001, that is, the energy spectrum of the radiated X-ray, when the X-ray filter or the X-ray grid which changes the X-ray energy spectrum is changed, the parameters are generally changed. It is therefore necessary to preliminarily measure VF and KF for combinations of all of the kinds of the X-ray filters and grids to be used and to store the results in a table. In FIGS. 7(A) to 7(C), the averaged output signal intensity Ic calculated by using the expression (4) for KF and VF derived by the above-mentioned methods is also shown.

It is understood from FIGS. 7(A) to 7(C) that the change in the averaged output signal intensity Ic in response to the change in the X-ray exposing area (Ax, Ay) is almost approximated by using the expression (4). Although it is approximated by the linear function in the expression (4) on assumption that the changes in the averaged output signal intensity Ic for the X-ray exposing area (Ax, Ay), the object thickness t, and the tube voltage V are linear, respectively, the approximation function is not limited to the example but may be replaced by a more proper one in accordance with a measurement value. For example, when the point spread function of the scattered X-ray is set to PSF(x, y), the approximation is performed by the normal distribution function as shown in the following expression (7).

$$PSF(x, y) = \frac{a}{2\pi b^2} \exp\left(\frac{x^2 + y^2}{2b^2}\right) \tag{7}$$

In this case, the approximation function shown in the expression (4) can be replaced by the following expression (8).

$$FF(A_x, A_y) = \frac{1 + 4a\phi(A_x/b)\phi(A_y/b)}{1 + 4a\phi^2(A_o/b)} \tag{8}$$

where, $\phi$ is the error function. Parameters a and b depend on the tube voltage V and the object thickness t, respectively, and are preliminarily calculated by executing the function fitting by the expression (8) to the plot values as shown in FIG. 7. Generally, although the approximation by the expression (8) is more accurate as compared with the approximation by the expression (4), the measurement of the parameters a and b is troublesome.

The deriver of the expressions 1 to 5 and the measuring methods of the parameters ap, bp, cp, am, bm, cm, KF, VF, KL, and VL in the expressions (1) to (5) have been described above with reference to FIGS. 4 to 7. Except for the above parameters, parameters FC and FI are included in the expression (1) which denote a coefficient for the camera mode and a coefficient for the I. I. mode of the X-ray I. I., respectively. FC and FI are equal to 1 in the standard camera mode and the standard I. I. mode, respectively. FC and FI can be easily measured by changing only the camera mode and the I. I. mode from the standard conditions under the standard condition or proper object thickness t, tube voltage V (for example, t=15 cm, V=90 kV, and the like) and proper kinds of the X-ray filter and X-ray grid, and measuring the rate of change of the averaged output signal intensity Ic.

In the expressions (1) and (6), one or both of the correction terms FF(V, t, Ax, Ay) and FL(V, t, L) for the change in the X-ray exposing area and the air gap can be omitted. That is, FF(V, t, Ax, Ay)=1 or FL(V, t, L)=1. Although the accuracy in the deriver of the object thickness t or the arithmetic operation of determining the X-ray radiographic conditions deteriorates in this case, the measurement mechanism for the X-ray exposing area or the air gap is not required, so that the apparatus construction can be relatively simplified. Especially, with respect to the correction term FL(V, t, L) of the air gap L, since the air gap L does not change in both of the fluoroscopic and radiographic exposures, the influence by the omission exerting on the arithmetic operation accuracy is small. For example, in case of omitting FL(V, t, L), as long as the difference between the fluoroscopic tube voltage V and the radiographic tube voltage V' is about within 20 kV, Q'Ω'G' determined by the expression (6) can be calculated within an error range of about 5%.

Although the levels shown in FIG. 4(A) are used as standard levels of the parameters in the embodiment, the invention is not limited to the levels. Especially, with respect to the standard levels of the air gap L and the X-ray exposing area (Ax, Ay), it is desirable to set to the levels which are most frequently used in the parameters, respectively. In this instance, the approximation error of FF(V, t, Ax, Ay) and FL(V, t, L) shown in the expressions (4) and (5) or the occurring frequency of the calculation error due to the omission can be suppressed.

As mentioned above, according to the X-ray apparatus of the embodiment, the relation of the object thickness and the signal intensity of the output image (averaged output signal intensity Ic) under the fluoroscopic conditions can be approximated by the expression (1), and values for specifying FC and FI as parameters in the expression (1), the parameters ab, bp, cp, am, bm, cm, KF, VF, KL, and VL in the expressions 2 to 5 for calculating Po(V), μ(V), FF(V, t, Ax, Ay) and FL(V, t, L), the imaging conditions for fluoroscopy and the imaging conditions for radiography instructed by the operator are stored in the tables 1114a to 1114c, the fluoroscopic conditions memory 1111, and the radiographic conditions memory 1113, respectively.

When the radiographic exposure is instructed, first, the object thickness calculation means 2201 calculates the thickness of the object on the basis of the imaging conditions for fluoroscopy.

After the radiographic tube voltage determination means 2202 determines the tube voltage of the X-ray tube 1001, the Q',Ω',G' calculation means 2203 determines the imaging conditions for radiography by executing simple calculations using the expressions (2) to (6) on the basis of the values stored in the tables 1114a to 1114c, the fluoroscopic conditions memory 1111 and the radiographic conditions memory 1113.

The saturation monitoring means 2204 discriminates whether there is any saturated item in the fluoroscopic conditions (setting values 3314 set by the automatic fluoroscopic control). If the fluoroscopic conditions are not saturated, the saturation monitoring means 2204 regards that the automatic exposure control for fluoroscopy is properly executed and the values Q'Ω'G' calculated by the Q'Ω'G' calculation means 2203 are used as they are. On the other hand, when the fluoroscopic conditions are saturated, the saturation monitoring means 2204 regards that the automatic exposure control for fluoroscopy is not properly executed, the value obtained by multiplying Q'Ω'G' by k (=Ico/Ic) is used so that the signal output of the radiographic image is equal to the proper level Ico.

In the Q'Ω'G' determination means 2205, each value of Q', Ω', and G' is calculated and recorded as the setting values 3315 set by the automatic exposure control for radiography and the X-ray radiographic exposure is performed by controlling the corresponding apparatuses by the controllers 1100 to 1106 and the amplifier 1107 on the basis of the setting values, that is, when the X-ray radiographic conditions are determined from the X-ray fluoroscopic conditions and the video signals at the time of the fluoroscopic exposure, the dose of the scattered X-rays which changes according to the change in the X-ray exposing area, the air gap, and the like can be accurately calculated by the simple functions. The X-ray radiographic conditions in which the change in the dose of the scattered X-rays is considered can be consequently determined. Thus, the X-ray radiographic exposure in which the influence by the X-ray scattering is eliminated can be more properly performed.

The X-ray radiographic exposure under the radiographic conditions that make output level of X-ray radiographic images proper can be performed in short time.

In the expression (6) for calculating the mAs value Q', the area Ω' of the iris, and the gain G' of the amplifier 1107 as the imaging conditions for radiography, the correction regarding the X-ray scattering is executed by the correction term consisting of FF(V, t, Ax, Ay) and FL(V, t, L) at the time of the fluoroscopic exposure and FF(V', t, Ax', Ay') and FL(V', t, L) at the time of the radiographic exposure. Consequently, the X-ray image of the object can be acquired under the radiographic conditions in which the influence by the X-ray scattering is considered.

Further, since the radiographic conditions arithmetic unit 1112 calculates the radiographic conditions by the values stored in the tables 1114a to 1114c, the fluoroscopic conditions memory 1111, and the radiographic conditions memory 1113 and by the expressions (2) to (6) based on the approximation expression of the output level shown in the expression (1), the X-ray radiographic exposure under the radiographic conditions that make output level of X-ray radiographic images proper can be performed with a small arithmetic operation amount, that is, in short time.

Since the radiographic conditions can be determined only by the product, the cheap arithmetic unit which does not have high-speed arithmetic ability can be used. Therefore, the X-ray apparatus can be manufactured at low costs.

Since the object thickness calculation means 2201 approximates the thickness of the object 1004 on the basis of the expression (1) and the tables 1114a and 1114b, for example, even if the intensity of the X-ray entering the X-ray detector at the time of the fluoroscopic exposure exceeds a limit in which the intensity can be properly detected, the object thickness can be accurately calculated.

Consequently, for example, even in a case where halation occurs in the X-ray image for fluoroscopy (fluoroscopic image), the object thickness can be accurately calculated, so that the radiographic conditions can be accurately determined.

Since the Q',Ω',G' calculation means 2203 calculates the radiographic conditions on the basis of the object thickness obtained from the calculation of the object thickness calculation means 2201, the radiographic conditions can be more properly calculated.

According to the X-ray apparatus of the embodiment, the functions peculiar to the apparatus are approximated by the expressions (4) and (5), and KF, VF, KL, and VL as parameters in the expressions (4) and (5) are stored in the table 1114c. Consequently, there are effects such that, for example, measurement for adjustment or the like in association with a periodic check or the like can be executed in short time and the adjustment of the apparatus can be easily performed by changing the above-mentioned parameters.

The saturation monitoring means 2204 monitors whether there is any saturated item in the fluoroscopic conditions or not. If there is a saturated item, the saturation monitoring means 2204 regards that the automatic exposure control for fluoroscopy is not properly executed and uses the value obtained by multiplying Q'Ω'G' by k (=Ico/Ic) as a radiographic condition so that the signal output of the radiographic image has the proper level Ico. For example, even when the gain of the amplifier 1107 at the time of the fluoroscopic exposure cannot be raised to a proper level due to the thickness of the object 1004, the radiographic conditions can be accurately calculated.

Further, there is also an effect such that when the standard levels (mAs value Q, iris Ω, gain G of amplifier, camera mode, I. I. mode, X-ray exposing area (Ax, Ay), and air gap L) shown in FIG. 4(A) are, for instance, levels which are most frequently used at the time of the fluoroscopic exposure, the error upon determination of the radiographic conditions due to the approximation error of the expressions (4) and (5) can be reduced.

The above-mentioned effects are especially excellent when the dose of scattered X-rays is large, that is, when the object is thick and the tube voltage of the X-ray tube is high.

As an example, a case in which the radiographic control was performed by using an acrylic board having the thickness of 28 cm as an object will be described hereinbelow. The fluoroscopic conditions of the tube voltage V of the X-ray tube=120 kV, and the X-ray exposing area Ax=Ay=7 inches, and the radiographic conditions of the tube voltage V' of the X-ray tube=108 kV and the X-ray exposing area Ax=Ay=12 inches were used. With respect to the other conditions (kind of the X-ray filter, kind of the X-ray grid, I. I. mode, iris, camera mode, gain of the amplifier, and air gap), the same conditions were used for both of the fluoroscopic and radiographic exposures. Especially, the same kind of the X-ray filter and the same kind of the grid as those in the experiments shown in FIGS. 4 to 7 were used. The I. I. mode, the iris, the camera mode, and the gain of the amplifier were set to the standard levels shown in FIG. 4(A). The air gap L was set to 25 cm.

Under the conditions, the radiographic conditions were obtained and the radiographic exposure was actually performed by the X-ray apparatus of the invention, and the fluoroscopic image and the radiographic image were compared.

As a result, when the averaged output signal intensity of the fluoroscopic image was set to 100%, the averaged output signal intensity of the radiographic image was about 95 to 105%. That is, the radiographic exposure could be performed with the error of about 5%.

On the contrary, when the radiographic control was performed by a conventional method as described in JP-A-62-15800 without considering the error of the dose of scattered X-rays at the times of both of the fluoroscopic and radiographic exposures, the averaged output signal intensity of the radiographic image was approximately 140 to 150% and an error of about 40 to 50% occurred. The main cause of such a large error is the change in the scattered X-ray dose in association with the change in the X-ray exposing area and the deviation of the air gap from the standard level. Since such a large error causes halation in the radiographic image, the radiographic exposure cannot be performed on the proper output level by the conventional method. However, it was recognized that the radiographic exposure can be performed on the proper output level by using the method of the apparatus shown in the invention.

Although the operation and effects of the X-ray apparatus were described in the embodiment, it is obviously understood that the invention is not limited to the X-ray apparatus but can be applied to a general X-ray fluoroscopic apparatus, an X-ray radiographic apparatus, an X-ray stereographic apparatus, a DSA apparatus (Digital Subtraction Angiographic apparatus), and the like.

Although the present invention realized by the inventors has been specifically explained on the basis of the embodiment of the invention for the first object of the invention, the invention is not limited to the embodiment of the invention but it is understood that many modifications and variations are possible without departing from the gist of the invention.

For example, although the system comprising the X-ray image intensifier 1007, the optical lens system 1008, and the television camera 1009 is used as an X-ray detector in the embodiment of the invention, the invention is not limited to the system. It is obviously understood that when the system is replaced by an X-ray detector using an X-ray flat panel detector or the like (imaging means) which can convert the X-ray signals directly to electric signals, the above-mentioned effects can be obtained. As an example of the X-ray flat panel detector, a method of using a TFT (Thin Film Transistor) is described in "Large Area, Flat-Panel, Amorphous Silicon Imagers" L. E. Antonuk, et al., SPIE, Vol. 2432, Physics of Medical Imaging, pp. 216 to 217 or the like.

Subsequently, arithmetic steps of three-dimensional image reconstruction as an embodiment of the X-ray apparatus regarding the second object of the invention will be shown. The relations of the X-ray absorption characteristics of the object in each radiographic direction, X-ray dose in each radiographic direction, and variance of data will be explained. The validity (effects) of the invention will be also described.

Figure 8:
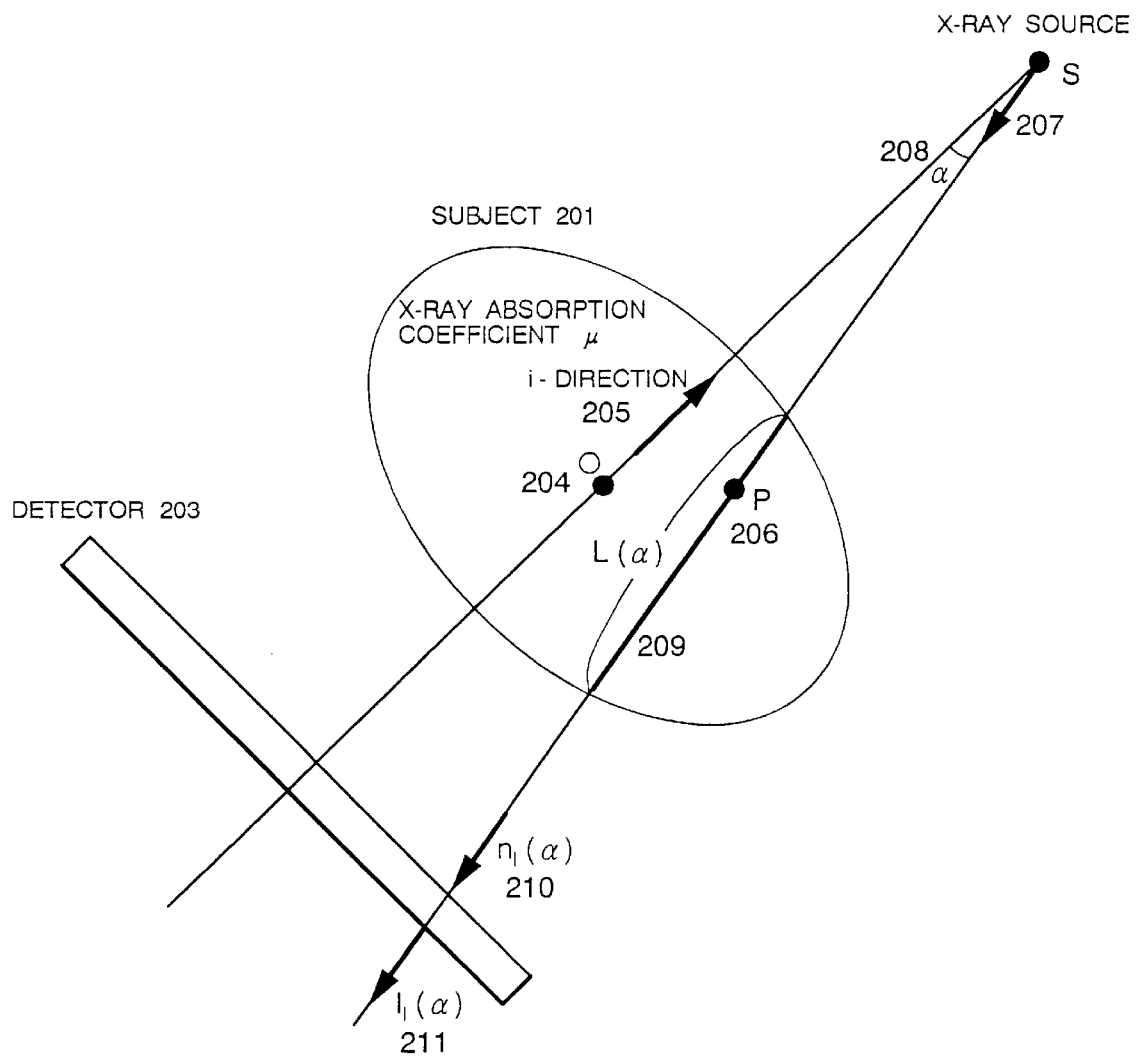
FIG. 8 is a diagram illustrating a radiographic model when radiographic exposure to an object is performed from a predetermined direction.

In X-ray rotatography, X-ray absorption projection images are acquired from various directions in order to obtain a three-dimensional image of X-ray absorption coefficients. The number of X-ray absorption projection images to be acquired is set to N. A model of radiography from an (i) direction is shown in FIG. 8. In FIG. 8, for simplicity, the paper face shows the rotation orbit surface of an X-ray tube and a section of the three-dimensional model is two-dimensionally displayed.

In FIG. 8, reference numeral 201 denotes an object; 202 an X-ray source S; 203 an X-ray detector; 204 a rotation center O; 205 an X-ray source direction when it is seen from the rotation center; 206 an aimed image reconstruction point P; 207 a direction of an aimed X-ray beam extending from the X-ray source S to the point P; 208 an angle α between the aimed X-ray beam and an X-ray beam extending to the rotation center; 209 a chord showing the aimed X-ray beam passing through the object 201; 210 an X-ray quantum number $n_i(\alpha)$ detected per channel by the X-ray beam from the (i) direction; and 211 a projection raw data output signal $I_i(\alpha)$ in the (i) direction. $L_i(\alpha)$ in FIG. 8 shows the length of the chord 209 and $\mu$ denotes the X-ray absorption coefficient of the object.

The projection raw data $I_i(\alpha)$ (where, i=1, . . . , a natural number of N) can be expressed by the following expression by using the X-ray quantum number $n_i(\alpha)$.

$$I_i(\alpha) = c_0 \cdot n_i(\alpha) + \epsilon$$

where, $c_0$ is a constant for controlling an iris and $\epsilon$ is circuit noise including noises occurring due to limitation of the number of bits at AD conversion.

Figure 9:
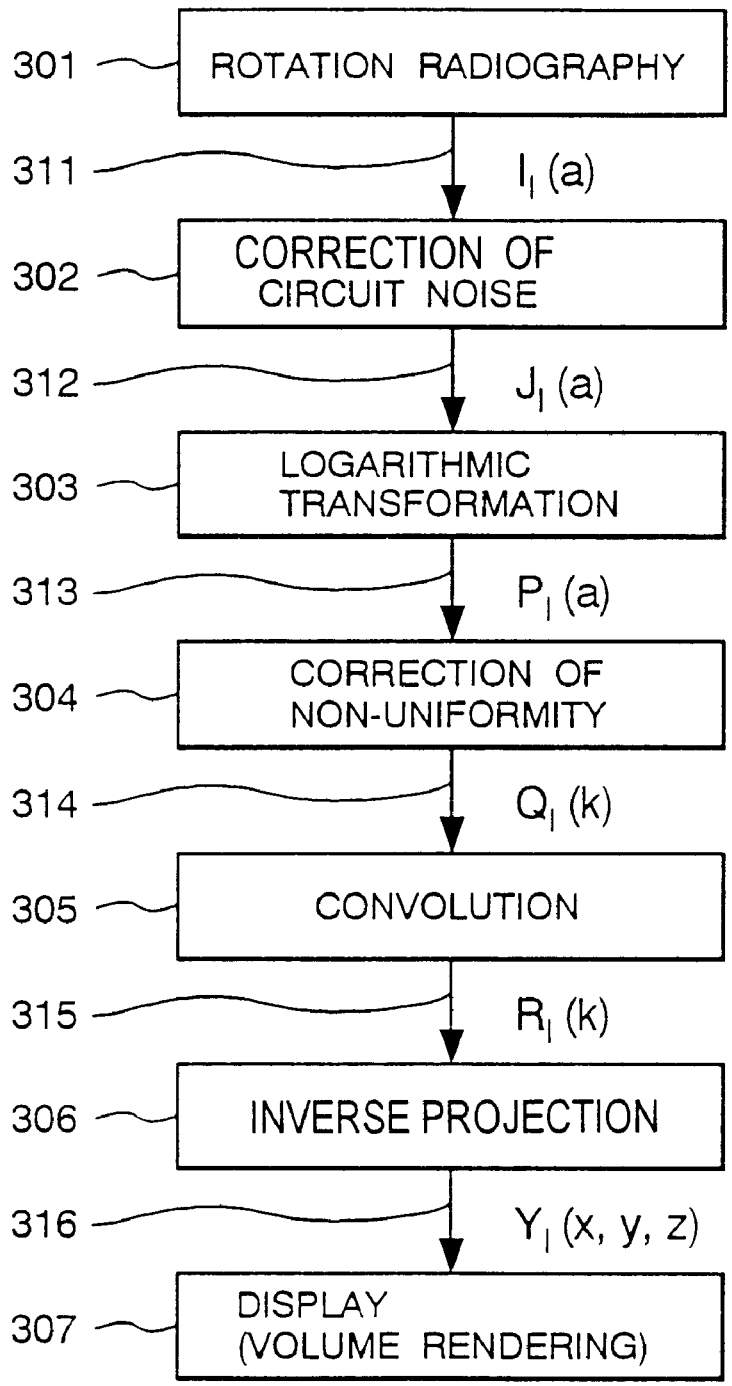
FIG. 9 is a diagram for explaining a flow of data processes in a cone-beam CT, starting from rotatographic exposure calculation of a level of a three-dimensional image and ending by display of the three-dimensional image.

FIG. 9 is a diagram for explaining the data processing flow starting from rotatographic exposure in a cone-beam CT, calculation of values for a three-dimensional image, and ending by display of the three-dimensional image. The flow of the data process will be described hereinbelow with reference to FIG. 9.

In FIG. 9, elements which are not directly related to the S/N ratio of the image such as positional relation of a measurement system or correction of distortion peculiar to the detector are omitted in order to simplify the description.

First, X-ray images of the object 201 are acquired while rotating the X-ray source 202 and the detector 203 around the object 201 (step 301).

In step 302, the average of noises is separately measured and an expectation $E(\epsilon)$ of the noises under the same conditions as those when the raw data $I_i(\alpha)$ is measured is calculated and is corrected by subtraction.

Noise components due to the limitation of the number of bits upon AD conversion cannot be corrected.

Subsequently, logarithmic transformation is performed (step 303).

Non-uniformity in beam intensity and in sensitivity of the detector of a projection image $P_i(\alpha)$ is corrected (step 304). The correction is performed by subtracting a sensitivity image, which is obtained by executing the logarithmic transformation to an image obtained by correcting the noises of the image acquired separately, by radiographic exposure without arranging the object from the projection image $P_i(\alpha)$. It is known from analysis results that non-uniformity correction data $Q_i(\alpha)$ is expressed by the following equations (9) and (10).

$$E\{Q_i(\alpha)\} = c_1 \cdot \mu \cdot L_i(\alpha) \tag{9}$$

$$V\{Q_i(\alpha)\} \approx \frac{c_0 \cdot c_1^2}{J_i(\alpha)} + \left\{\frac{c_1}{J_i(\alpha)}\right\}^2 \cdot V(\varepsilon) \tag{10}$$

Subsequently, convolution is executed (step 305).

Expectation and variance as the results of the convolution are expressed by the following equations (11) and (12), respectively.

$$E\{R_i(k)\} = c_1 \cdot \mu \cdot \sum_{k'=-\infty}^{\infty} L_i(k') w(k' - k) \tag{11}$$

$$V\{R_i(k)\} = \sum_{k'=-\infty}^{\infty} w^2(k') \cdot \left[\frac{c_0 \cdot c_1^2}{J_i(k' + k)} + \left\{\frac{c_1}{J_i(k' + k)}\right\}^2 \cdot V(\varepsilon)\right] \tag{12}$$

Subsequently, inverse projection is executed (step 306). Generally, when the number of projection images used for the image reconstruction is set to N, a reconstruction image at a point (x, y, z) in XYZ space is set to Y(x, y, z) and corresponding convolution data is described as $c_1 \mu S_i$ (x, y, z) for convenience, the reconstruction image Y(x, y, z) is obtained by the following expression (13), which does not depend on the distribution of the X-ray dose.

$$Y(x, y, z) = \frac{c_1 \cdot \mu}{N} \cdot \sum_{i=1}^{N} S_i(x, y, z) \tag{13}$$

On the other hand, relative noise of the image is defined by the left term of the following equation (14), and the contents are shown in the right term. The first term of the numerator of the expression (14) is not influenced by the circuit noise and the second term is influenced by the circuit noise.

$$\frac{\sigma\{Y(x, y, z)\}}{Y(x, y, z)} = \frac{\sqrt{\sum_{i=1}^{N}\left[\frac{1}{n_i(x, y, z)} + \frac{1}{\left\{n_i(x, y, z) \cdot \frac{c_0}{\sigma(\varepsilon)}\right\}^2}\right]}}{\mu \cdot \sum_{i=1}^{N} S_i(x, y, z)} \tag{14}$$

The denominator of the expression (14) is a term depending on only the X-ray absorption characteristic of the object and a convolution filter so that it has no relation with the measurement method. On the other hand, the numerator of the expression (14) depends on an X-ray quantum number $n_i(x, y, z)$ (where, n=1, . . . , natural number of N) measured by radiographic exposures from respective directions, circuit noise standard deviation $\sigma_i(\epsilon)$ and a constant $c_0$ depending on the circuit gain or the like. $n_i(x, y, z)$ is obtained by the following expression (15).

$$n_i(x, y, z) = n_{oi} \cdot exp\{-\mu \cdot L_i(x, y, z)\} \tag{15}$$

In the expression (15), $n_{0i}$ is an X-ray quantum number at the position where the thickness of the object is zero from the (i) direction, which is in proportional to the X-ray dose used for the radiographic exposure from the (i) direction.

On the other hand, as $n_{0i}$ is not changed in a conventional cone-beam CT, $n_{0i}$ is evenly distributed and constant irrespective of i and is expressed by the following expression (16).

$$n_{0i} = n_0 = \frac{n_T}{N} \tag{16}$$

where, $n_T$ is an X-ray dose sum.

On the contrary, in the invention, the dose of X-rays for radiography is distributed according to the object, $n_{0i}$ which reduces the expression (14) is given under the conditions of the following expression (17).

$$n_T = \sum_{i=1}^{N} n_{oi} \tag{17}$$

When the second term of the route in the numerator of the expression (14) can be small enough to be ignored as compared with the first term, that is, when the standard deviation $\sigma(\epsilon)$ of the circuit noise is small enough to be ignored as compared with $c_0$, $n_{0i}$ which makes the expression (14) smallest is analytically expressed from the Schwarz's inequality by the following expression (18).

$$n_{0i} = \frac{n_T \cdot \frac{1}{\sqrt{\exp\{-\mu \cdot L_i(x, y, z)\}}}}{\sum_{i=1}^{N} \frac{1}{\sqrt{\exp\{-\mu \cdot L_i(x, y, z)\}}}} \quad (18)$$

As obviously understood from the expression, in order to optimize the S/N ratio of a certain aimed point, in place of using the expression (16), it is sufficient to distribute the X-ray dose which is inproportional to the square root of the X-ray transmitted rate by the expression (18). The minimum in this case is obtained from the following expression (19).

$$\min \sigma\{Y(x, y, z)\} = \frac{c_1}{N \cdot \sqrt{n_T}} \cdot \sum_{i=1}^{N} \frac{1}{\sqrt{\exp\{-\mu \cdot L_i(x, y, z)\}}} \quad (19)$$

The ratio of the minimum of the expression (19) to the value $\sigma_c$ according to a conventional method is calculated by the following expression (20).

$$\frac{\min \sigma\{Y(x, y, z)\}}{\sigma_c\{Y(x, y, z)\}} = \frac{\sum_{i=1}^{N} \frac{1}{\sqrt{\exp\{-\mu \cdot L_i(x, y, z)\}}}}{\sqrt{N} \cdot \sqrt{\sum_{i=1}^{N} \exp\{-\mu \cdot L_i(x, y, z)\}}} \quad (20)$$

As obviously understood from the above description, by distributing the X-ray level inproportional to the square root of the X-ray transmitted rate to each of the radiographic exposures, the relative noise shown by the expression (14) is reduced and the image noises can be reduced close to an ideal minimum. Information of the X-ray transmitted rate of the aimed position can be acquired from the ratio of the radiographic image acquired (measured) by performing radiographic exposure to an arranged object to a blank image acquired under the same X-ray conditions without arranging the object.

With respect to the case where the second term cannot be ignored, the effect was confirmed by simulation.

Figure 10A:
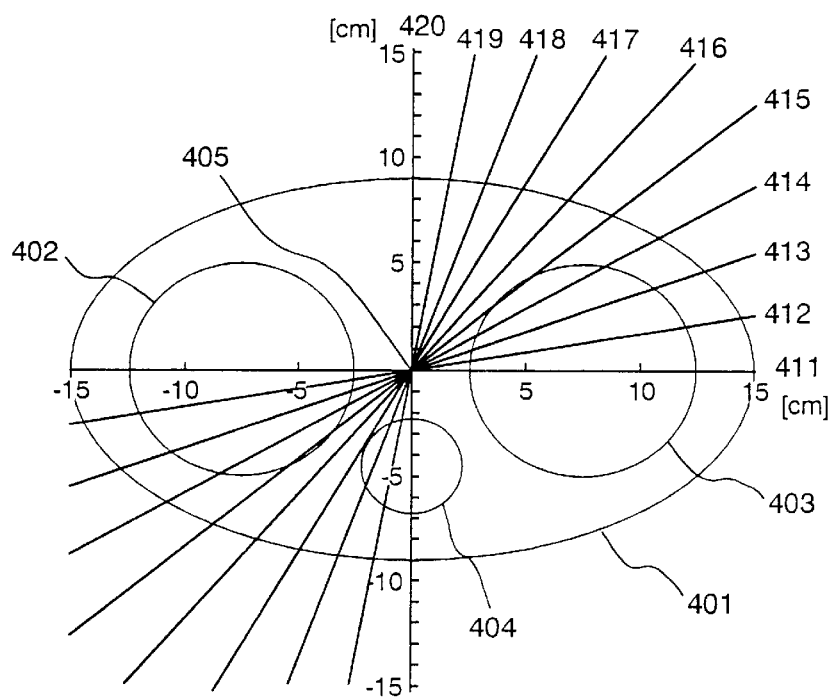
FIGS. 10A and 10B are diagrams for explaining a method of assuming and simulating the shape of an object when the second term cannot be ignored.
Figure 10B:
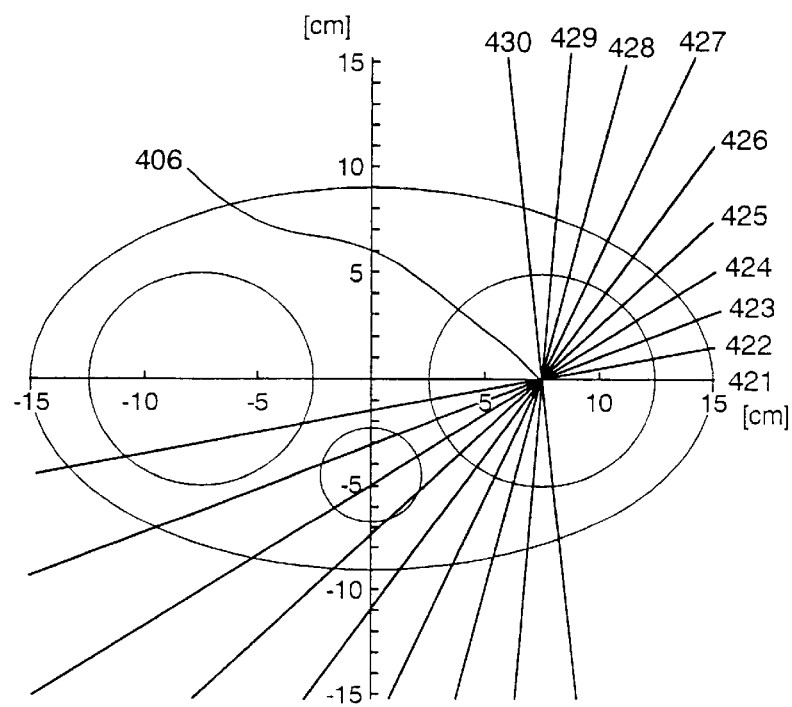

FIGS. 10A and 10B are diagrams for explaining a method of the simulation. FIGS. 10(A) and 10(B) show X-ray beams passing aimed positions of two kinds in an object of the shape stimulating the chest.

The slice shape of the simulated object shown in FIGS. 10A and 10B has an ellipse outline 401 and has therein two circular areas 402 and 403 simulating the lungs which do not absorb and a circular area 404 stimulating the backbone. It is assumed that the shape of the object is symmetrical with respect to the spindle. An aimed position is set to a rotation center 405 in FIG. 10A and is set to the center position 406 of one of the lungs in FIG. 10B. Linear lines 411 to 420 in FIG. 10A show X-ray beams passing the aimed area 405 at intervals of 10 in a range where the rotation angle of the X-ray source is from 0 to 90. On the other hand, linear lines 421 to 430 in FIG. 10B show X-ray beams passing the aimed area 406 at intervals of 10 in a range where the rotation angle of the X-ray source is from 0 to 90. The rotation radius of the X-ray source is 72 cm.

Figure 11A:
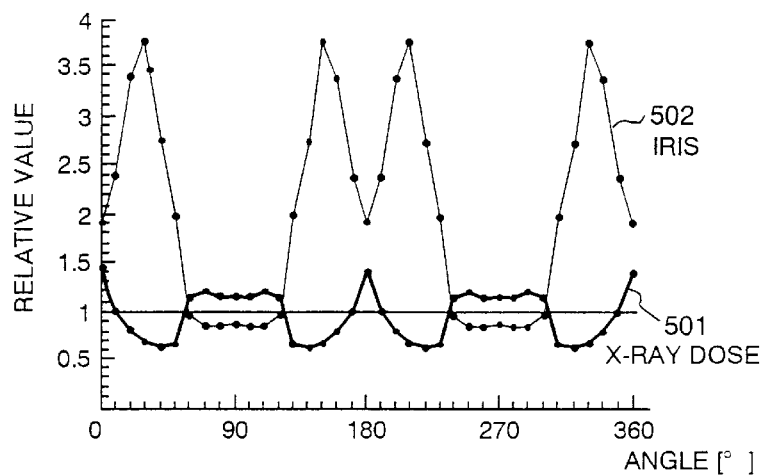
FIGS. 11A–11C are diagrams for explaining an effect of the invention when the second term cannot be ignored.

A broken line 501 in FIG. 11A shows the X-ray dose which is displayed in such a manner that radiographic exposure to the object of FIGS. 10A and 10B is simulated every 10 by a rotation of the X-ray source in FIG. 10, the distribution result of the X-ray dose when the radiographic exposure with the X-ray dose inproportional to the square root of the X-ray transmitted rate is performed is obtained, and the average of the X-ray dose is standardized to 1. A range of 6.85 toward both sides from the center of the visual field in the data of a plan is used as an aimed area and the minimum in the aimed area is used as an X-ray transmitted rate. The standard deviation of the circuit noise is set to 1, the full scale of an image is set to 1023, and the X-ray quantum number per pixel is used as a parameter. In the simulation result, the X-ray level has a steep peak at about 0 and a wide peak ranging from 60 to 120. Since the object is symmetrical, the data is almost symmetrical with respect to angles of multiples of 90.

A broken line 502 in FIG. 11A shows an example of setting values of efficiency of an iris. The result of setting the maximum in the aimed area so as not to exceed a saturation level of a measurement unit and so as to be constant is shown by relative values. It is understood that the broken lines 501 and 502 show movements independently. It shows that the optimum levels of the X-ray dose and the efficiency of the iris can be independently determined.

Figure 11B:
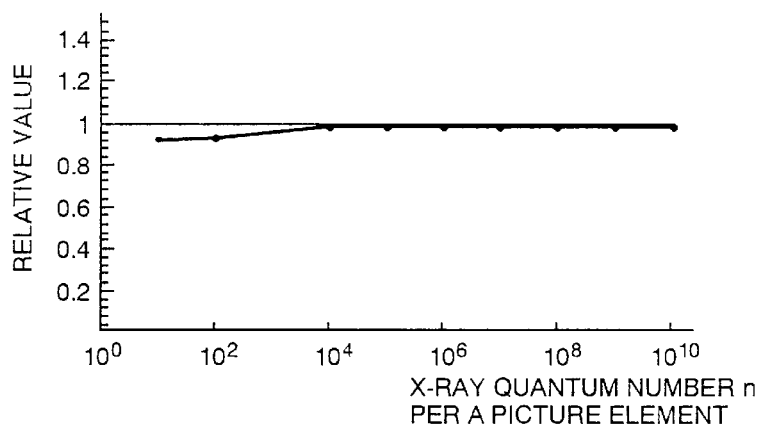
Figure 11C:
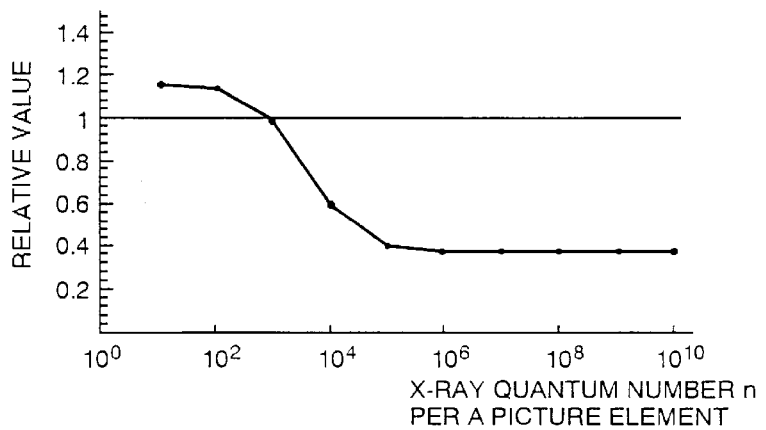

Each of FIGS. 11B and 11C shows the ratio of image noise obtained by the above-mentioned method to noise obtained by a conventional method with respect to the aimed point 405 in the center of the visual field and the aimed point 406 in the lung.

According to the present method, although there is little difference from the conventional method with respect to the center of the visual field, the noise remarkably is reduced in the lung as compared with the conventional method.

As mentioned above, it is understood that even in the case where the circuit noise, that is, the second term of the expression (13) cannot be ignored, the effect of the X-ray distribution according to the above-mentioned method is very large.

The number of images used and characteristics will be described hereinbelow.

In case of using an image acquired just before, since image data of one image is used, a control circuit is easily realized. When an angle pitch in the rotatographic exposure is small, the image functions as a predicted image with sufficient accuracy.

When total two images of the image acquired just before and an image before the image are used, a predicated image is formed by using present averaged change rate information. By predicting the characteristic, the accuracy of prediction of the next image is improved as compared with the case of using only the image acquired just before. As a result, the contrast resolution of the image is improved.

When total three images of an image acquired just before, an image acquired before the image, and an image two images before are used, the predicted image is formed by estimating change in the rate of change and the characteristic is predicted. In this case, since the prediction accuracy is further improved as compared with the case of using only two images, the contrast resolution of the image can be further improved. Even in the case where the angle pitch in the rotatographic exposure is large, it functions as the predicted image with sufficient accuracy.

Embodiments of the invention will be described in detail hereinbelow with reference to the drawings.

In all of the drawings for explaining the embodiments of the invention, components having the same function are designated by the same reference numerals and the repetitive description is omitted.

(First Embodiment)

Figure 12A:
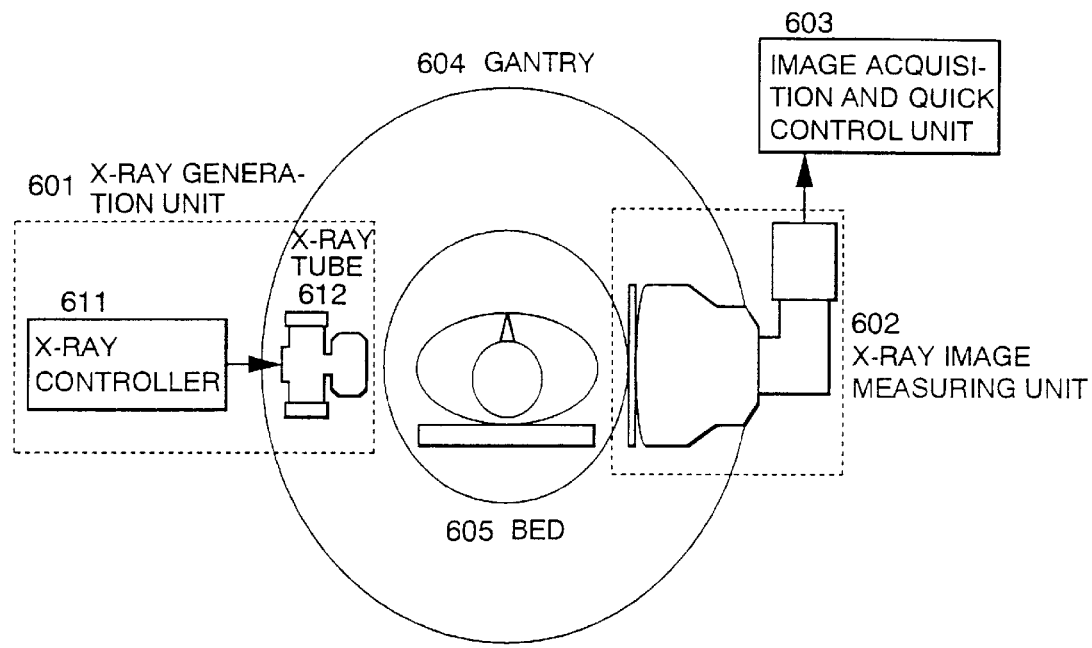
FIGS. 12A and 12B are diagrams for explaining a schematic construction of a rotatographic apparatus as an X-ray apparatus of the first embodiment of the invention.
Figure 12B:
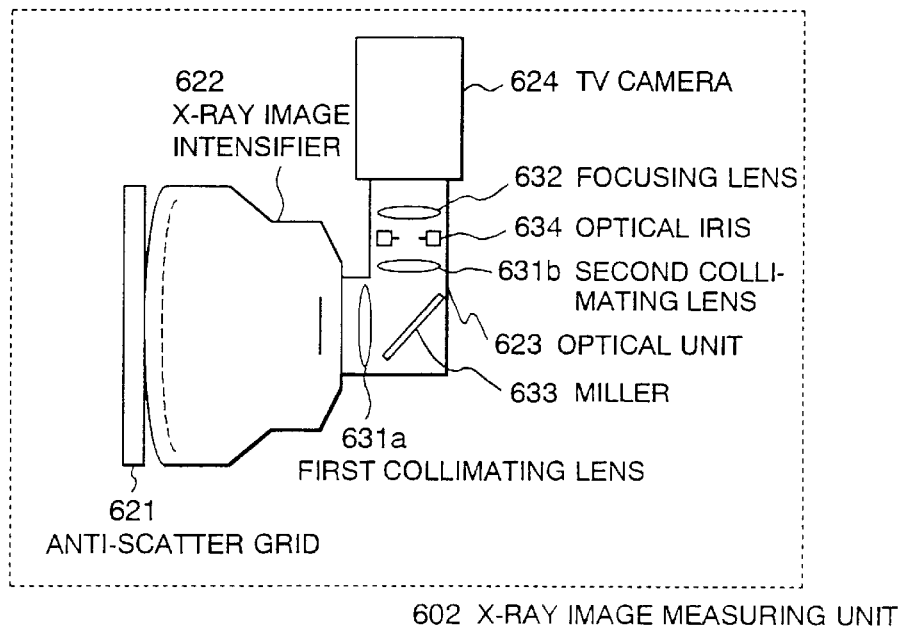

FIGS. 12A and 12B are diagrams for explaining a schematic construction of a rotatographic apparatus as an X-ray apparatus of the first embodiment of the invention. Specifically, FIG. 12A is a diagram showing a schematic construction of the rotatographic apparatus and FIG. 12B is a diagram for explaining a schematic construction of an image measuring unit.

In FIGS. 12A and 12B, reference numeral 601 denotes an X-ray generation unit (X-ray radiation means); 602 an image measuring unit (imaging means); 603 an image acquisition and quick control unit (radiation dose control means); 604 a gantry (rotating means); 605 a bed; 611 an X-ray controller; 612 an X-ray tube; 621 an anti-scatter grid; 622 an X-ray image intensifier (hereinbelow, described as an "X-ray I. I."); 623 an optical unit; 624 a television camera; 631*a* a first collimating lens; 631*b* a second collimating lens; 632 an optical iris as an example of signal control means; 633 a mirror; and 634 a focusing lens.

In FIG. 12A, the X-ray generation unit 601 has the X-ray controller 611 and the X-ray tube 612. The X-ray controller 611 is connected to the image acquisition and quick control unit 603 and the X-ray tube 612 and supplies a tube voltage to the X-ray tube 612 on the basis of a control signal from the image acquisition and quick control unit 603. The X-ray tube 612 is fixed to the gantry 604.

The image measuring unit 602 is constructed by the anti-scatter grid 621, the X-ray I. I. 622, the optical unit 623, and the television camera 624. The image measuring unit 602 is fixed to the gantry 604 so as to face the X-ray tube 612.

The image acquisition and quick control unit 603 is connected to the television camera 624 and acquires X-ray images which are converted to digital signals (digital information) by the television camera 624. The image acquisition and quick control unit 603 calculates radiographic conditions and controls the gantry, the optical iris, the television camera, and the X-ray generation unit. The image acquisition and quick control unit 603 has construction and functions peculiar to the invention. The details will be described hereinlater.

The gantry 604 rotates the X-ray tube 612 and the image measuring unit 602 around the bed 605 by a power of a rotation drive apparatus (not shown).

In FIG. 12B, the anti-scatter grid 621 is a known radiation shielding grid and is arranged on the input face of the X-ray I. I. 622.

The X-ray I. I. 622 is a known X-ray I. I., which converts an X-ray image entered from the input face into an optical image and outputs the optical image from the output face.

The optical unit 623 is constructed by the first collimating lens 631*a*, the second collimating lens 631*b*, the focusing lens 632, the mirror 633, and the optical iris 634 which construct a tandem lens system. In the optical unit, the first collimating lens 631*a* is arranged on the side of the output face of the X-ray I. I. 622 and receives the optical image transmitted from the output face. The optical unit 623 is a known optical system.

The television camera 624 is a known television camera using a CCD image sensor device as an image pickup device and is arranged on the focusing lens 632 side of the optical unit 623.

Since the radiographic operation in the rotatographic apparatus of the first embodiment is the same as a radiographic operation of a known rotatographic apparatus with respect to a point that it is performed on the basis of a control signal of the image acquisition and quick control unit 603, the description is omitted here.

Figure 13:
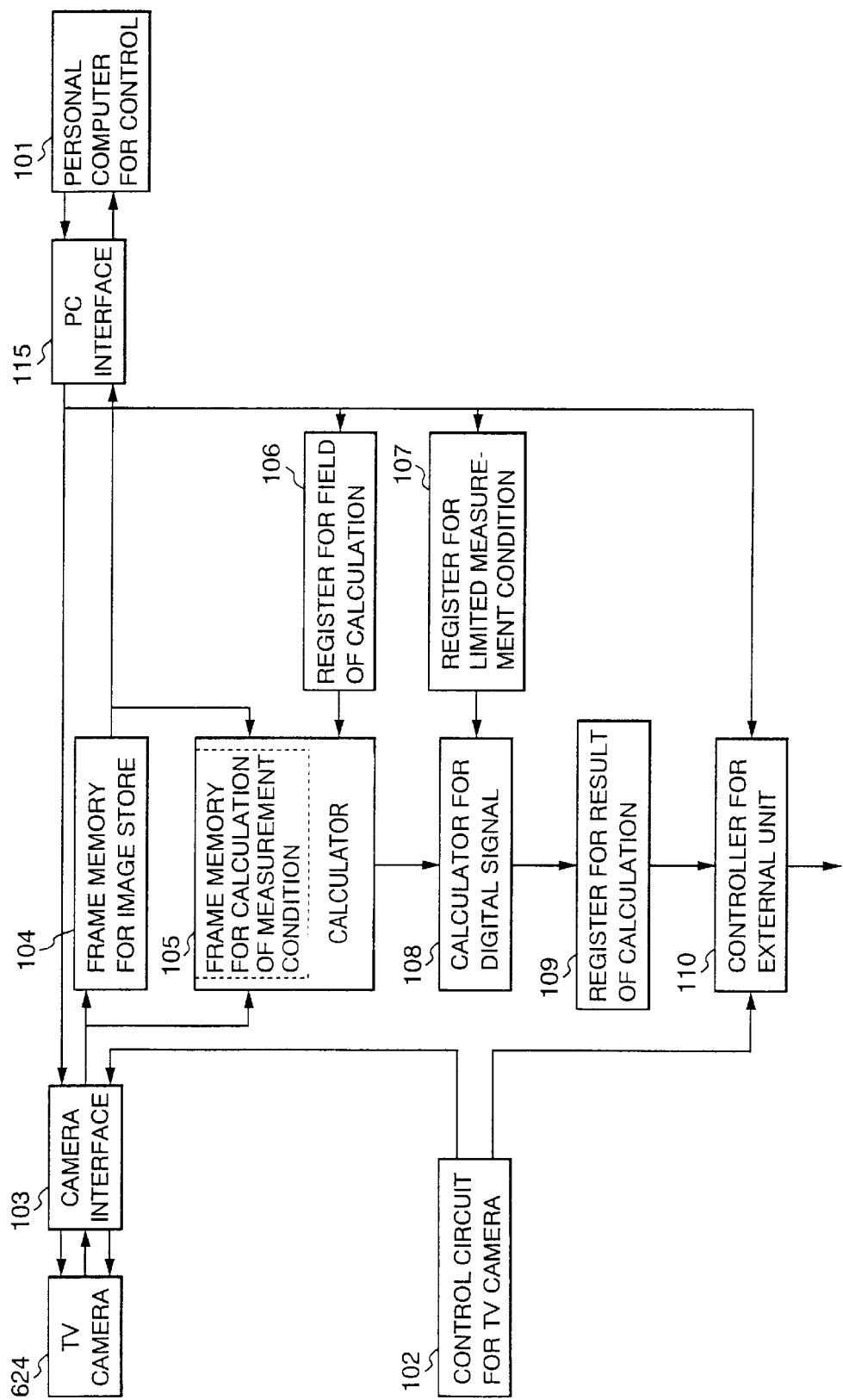
FIG. 13 is a block diagram for explaining a schematic construction of an image acquisition and quick control unit of the first embodiment.

FIG. 13 is a block diagram for explaining the schematic construction of the image acquisition and quick control unit of the first embodiment. Reference numeral 101 denotes a personal computer (PC) for control; 102 a control circuit for synchronized camera signal; 103 a camera interface; 104 a frame memory for image storage; 105 a calculator for images (X-ray image predicting means); 106 a register for field of calculation; 107 a register for limited measurement condition (permissible range storage means); 108 a calculator for digital signal (DSP); 109 a register for result of calculation; 110 a controller for external unit; and 115 a PC interface.

In FIG. 13, the PC 101 for control is a known information processor, which controls the television camera 624, the X-ray controller 611, the gantry 604, the rotation drive apparatus (not shown), and displays a radiographic image, a three-dimensional reconstructed image, and the like.

The control circuit 102 for synchronized camera signal is a known control circuit for synchronized television camera signal and controls the imaging mode, the iris, and the like of the television camera 624 via the camera interface 103. In the embodiment, the operation mode of the television camera 624 is 12 bits, 40 MHz, and 512×512 pixels.

The camera interface 103 is a known interface circuit for television camera which converts the signal format of the image acquisition and quick control unit 603 into the signal format of the television camera 624. The camera interface 103 is therefore connected to each of the PC interface 115, the frame memory 104 for image storage, the calculator 105, the control circuit 102 for synchronized camera signal, and the television camera 624.

The frame memory 104 for image storage is, for example, a known frame memory using a semiconductor memory and has a capacity which can continuously collect 288 or more images each having 512×512 pixels and 12 bits in the embodiment.

The calculator 105 for images includes a frame memory for calculation of measurement conditions and an addition and subtraction means with weighted coefficient on images for executing calculation to an image stored in the frame memory for calculation, and acquires the next predicted image. The calculator 105 for images is consequently connected to the camera interface 103, the frame memory 104 for image storage, the register 106 for field of calculation, and the DSP 108.

The register 106 for field of calculation is a known register, for example, which stores a field of calculation inputted from the PC 101 for control by the examiner and is connected to the calculator 105 for images and the PC interface 115.

The register 107 for limited measurement condition is a register for storing initial and present values and maximum and minimum levels of the X-ray pulse width, and initial and present values and maximum and minimum levels of the optical iris. For example, a known semiconductor memory is used as the register 107. The register 107 for limited measurement condition is consequently connected to the PC interface 115 and the DSP 108.

The DSP 108 is a known digital signal processor, which calculates the maximum and minimum pixel values indicative of the image level of the field of calculation, with respect to the present image and an image acquired by the calculator for images. The DSP 108 is, therefore, connected to the calculator 105 for images, the register 107 for limited measurement condition, and the register 109 for result of calculation. The details of the DSP 108 will be described hereinlater.

The register 109 for result of calculation is constructed by, for example, a known semiconductor memory and stores the X-ray pulse width and the iris for the next image acquisition determined by the DSP 108.

The controller 110 for external units controls the X-ray controller 611, the rotation controller of the drive device of the gantry 604, and the like. A controller for the X-ray generator included in the controller 110 for external units outputs a TTL level pulse having the pulse width same as the X-ray pulse width. Output timing is controlled by a CPU (not shown). The pulse width in case of continuous measurement ranges from 0.3 ms to 5 ms. Single measurement is also possible. A controller for an iris device included in the controller 110 for external units outputs a direct current voltage corresponding to an iris value to an optical iris device. A control voltage in this case ranges from 5.0V to 10.0V. When the voltage is 5.5V or lower, the iris is open (ϕ78 or larger). When the voltage is 10.0V, the iris is shut to ϕ10 or lower.

Figure 14:
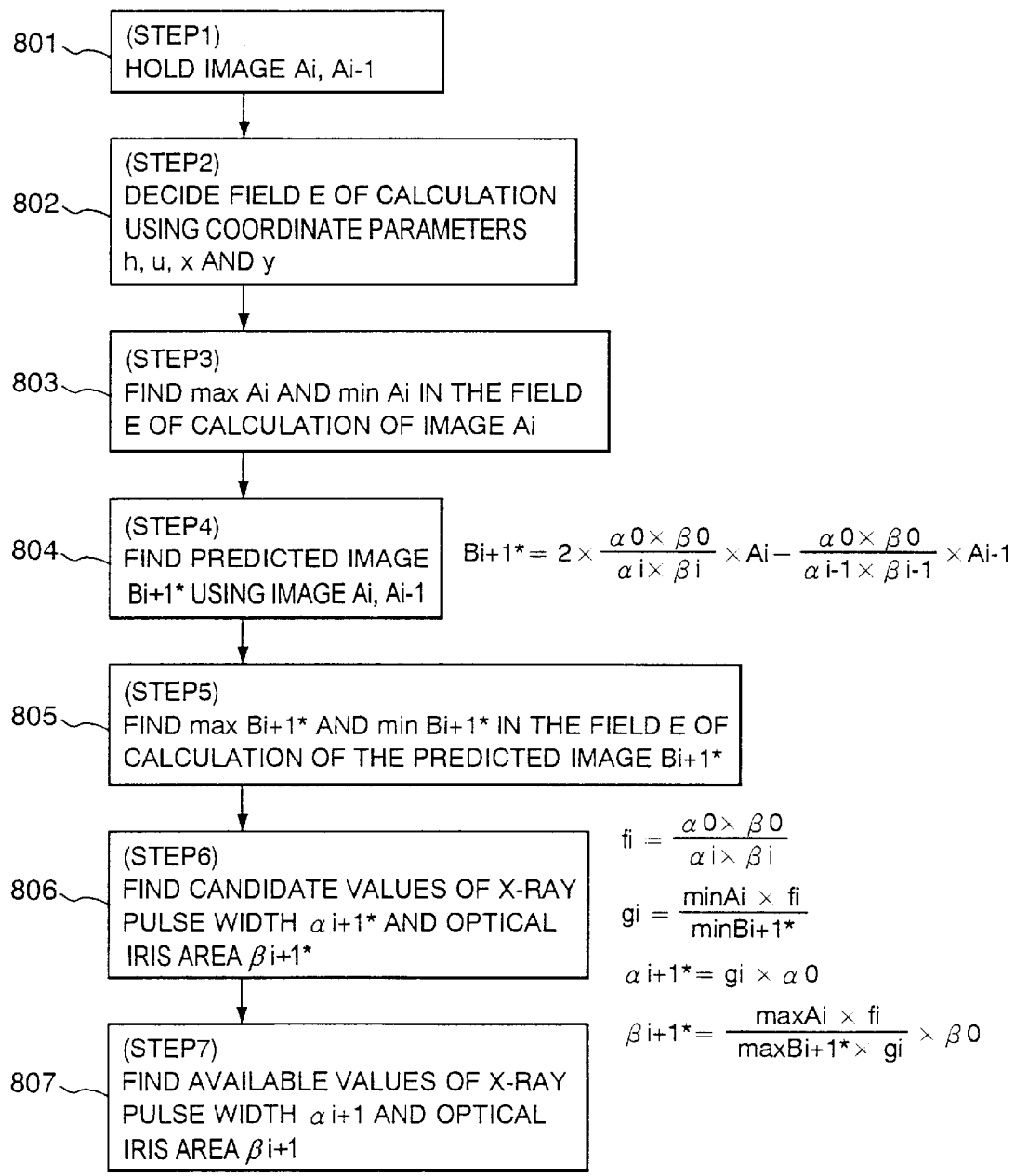
FIG. 14 is a flow for explaining the operation of the image acquisition and quick control unit of the first embodiment.

FIG. 14 shows a flow for explaining the operation of the image acquisition and quick control unit of the first embodiment. The operation of the image acquisition and quick control unit according to the embodiment shown in FIG. 13 will be described hereinbelow with reference to FIG. 14.

First, before starting measurement, rotation control operation of the gantry is executed by the controller 110 for external unit in the image acquisition and quick control unit. That is, the rotating operation of the gantry which is under stationary condition is started and rotatographic exposure is started when the gantry passes a predetermined position at a predetermined time. In typical measurement, 288 digital signal images (Ak, k =0, . . . , 277) each having 512×512 pixels, 12 bits, and 40 MHz of a CCD camera are continuously collected at a speed of 60 frames per second. For example, Ao denotes an image which is collected first.

The frame memory for calculation in the calculating circuit 105 always overwrites and holds three images of a present image, that is, an image acquired just before, and an image one frame before, and an image two frames before. The frame memory for calculation always holds an image acquired by the calculation for images, that is, the predicted image.

Figure 15:
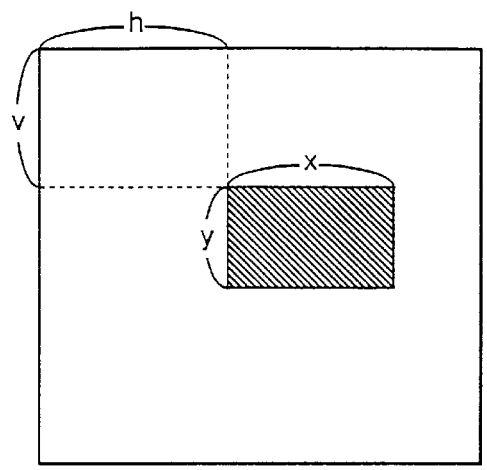
FIG. 15 is a diagram for explaining parameters regarding a field of calculation designated by a variable of a register for field of calculation.

The register 106 for field of calculation designates a calculation field to which calculation, which will be described hereinlater, is executed by four variables. FIG. 15 is a diagram for explaining parameters regarding the calculation field.

An imaging process performed by the image acquisition and quick control unit will be described hereinbelow. The process relates to an example of calculation in the case where radiographic conditions of the next image, that is, an X-ray pulse width $\alpha_{i+1}$ and an optical iris (area) $\beta_{i+1}$ are determined in a real time manner when an (i)th image $A_i$ is measured.

(1) First step: Two images of the present image $A_i$ and an image $A_{i-1}$ one frame before are held in the frame memory for calculation of measurement condition in the calculator 105 (step 801) in order to predict the next image by using the two images.

(2) Second step: A calculation area E (m, n) designated by four coordinate parameters h, v, x, and y shown in FIG. 15 by the register 106 for field of calculation are determined (step 802). A representative example of the calculation area is an area of 384 pixels (horizontal direction)×256 pixels (vertical direction) in the center part of the image. The calculation area is set so that a radiographic region which is desired to have high picture quality is included and a peripheral part such as a part in which halation occurs is not included.

(3) Third step: The maximum level max$A_i$ and the minimum level min$A_i$ of the calculation area in the image $A_i$ in the frame memory for calculation of measurement condition are obtained (step 803). For example, minAo denotes the minimum level of the calculation area in an image Ao.

(4) Fourth step: An image to be acquired next, that is, a predicted image (predicted X-ray image) $B_{i+1}^*$ is obtained by using the image $A_i$ and the image $A_{i-1}$ (step 804).

With respect to a method of calculating the predicted image $B_{i+1}^*$, a variable coefficient $f_i$ for acquiring an image when radiographic exposure under initial conditions (standard conditions) is assumed is obtained. The calculation method is expressed by the following expression (21).

$$f_i = \frac{\alpha_0 \cdot \beta_0}{\alpha_i \cdot \beta_i} \qquad (21)$$

where, $\alpha_0$ is an initial value of the X-ray pulse width, $\beta_0$ is an initial value of the iris, $\alpha_i$ is the present X-ray pulse width, and $\beta_i$ is the present iris. It is assumed that $f_{i-1}$ is preliminarily obtained by the following expression (22).

$$f_{i-1} = \frac{\alpha_0 \cdot \beta_0}{\alpha_{i-1} \cdot \beta_{i-1}} \qquad (22)$$

where, $\alpha_{i-1}$ is the X-ray pulse width of one frame before and $\beta_{i-1}$ is the iris of one frame before.

The image to be acquired, that is, the next image is predicted by direct extrapolation by using the two images of an image acquired just before and an image acquired before the image. A calculation in this case is executed by the following expression (23).

$$B_{i+1}^* = 2 \times f_i \cdot A_i - f_{i-1} \cdot A_{i-1} \qquad (23)$$

Consequently, the above-mentioned predicted image $B_{i+1}^*$ can be calculated.

(5) Fifth step: The maximum max$B_{i+1}^*$ and the minimum min$B_{i+1}^*$ of the calculation area in the predicted image $B_{i+1}^*$ are obtained (step 805).

(6) Sixth step: In the DSP 108, a correction coefficient $g_i$ for the initial X-ray pulse width is obtained by the following expression (24). A candidate $\alpha_{i+1}^*$ for X-ray pulse width of the next radiographic exposure is obtained by the following expression (25). After that, a candidate $\beta_{i+1}^*$ for iris is subsequently obtained by the following expression (26). The expression (24) shows a calculation of the ratio of the first transformed level to the second transformed level.

$$g_i = \sqrt{\frac{\min A_0}{\min B_{i+1}^*}} \qquad (24)$$

$$\alpha_{i+1}^* = g_i \cdot \alpha_0 \qquad (25)$$

$$\beta_{i+1}^* = \frac{\max A_i \cdot f_i}{\max B_{i+1}^* \cdot g_i} \cdot \beta_0 \qquad (26)$$

The above expression (26) intends to set the iris so that the maximum of the image is not changed even if the X-ray transmitted rate of the object and the X-ray dose are changed.

Figure 16:
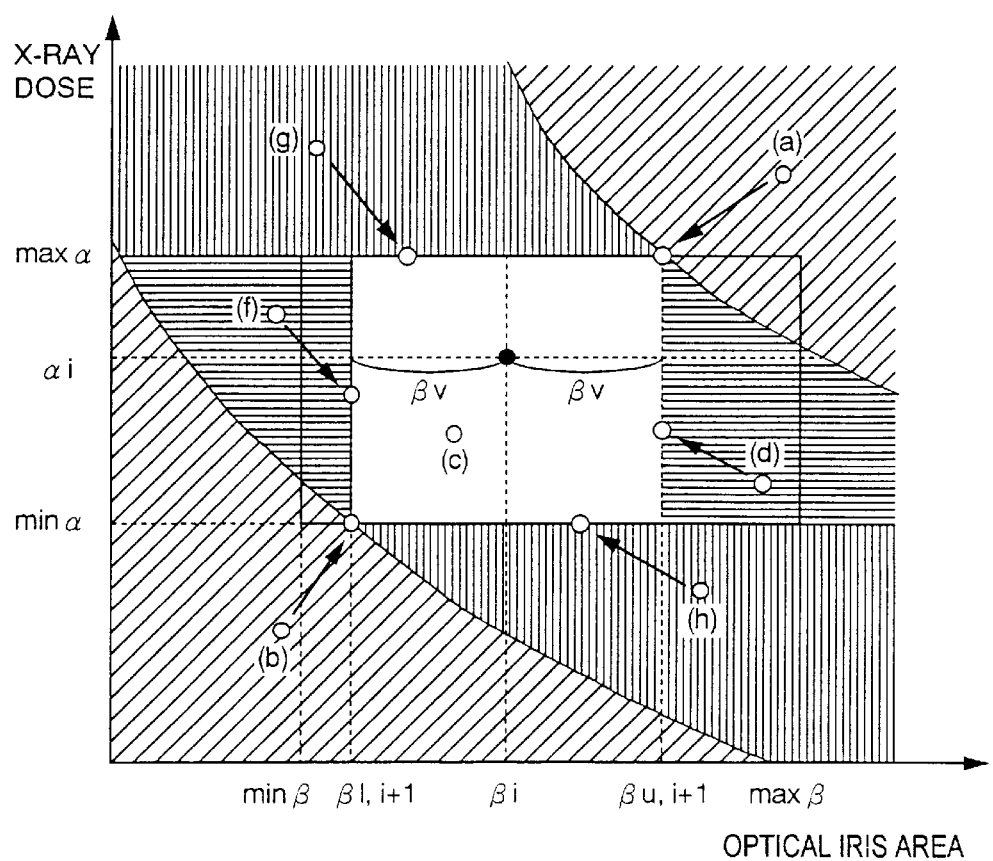
FIG. 16 is a diagram for explaining specific discriminating conditions in a DSP.

(7) Seventh step: In the DSP 108, the relations of $\alpha_{i+1}^*$, the maximum level max$\alpha$, and the minimum level min$\alpha$ regarding the X-ray pulse width stored in the register 107 for limited measurement condition are discriminated. The relations of $\beta_{i+1}^*$ and the maximum level max$\beta$, the minimum level min$\beta$, and a changeable maximum change amount $\beta v$ in one frame time regarding the iris are also discriminated. Specific discrimination conditions are (a) to (h) shown below. The X-ray pulse width $\alpha_{i+1}$ and the iris $\beta_{i+1}$ of the next image which can be realized are determined from the results. The state of the distribution is shown in FIG. 16. (a) to (h) shown below correspond to areas (a) to (h) in FIG. 16, respectively.

$$\beta_{u,i+1} = \min[\max\beta, \beta_i + \beta_v] \quad (27)$$

$$\beta_{l,i+1} = \max[\min\beta, \beta_i - \beta_v] \quad (28)$$

$$\gamma_{i+1}^* = \alpha_{i+1}^* \cdot \beta_{i+1}^* \quad (29)$$

(a) When $\gamma_{i+1}^* \geq \max \alpha \cdot \beta_{u,i+1}$, $$\beta_{i+1} = \beta_{u,i+1} \quad (30)$$

$$\alpha_{i+1} = \max \alpha \quad (31)$$

(b) When $\gamma_{i+1}^* \leq \min \alpha \cdot \beta_{l,i+1}$, $$\beta_{i+1} = \beta_{l,i+1} \quad (32)$$

$$\alpha_{i+1} = \min \alpha \quad (33)$$

(c) When $\min \alpha \leq \alpha_{i+1}^* \leq \max \alpha$ and $\beta_{l,i+1} \leq \beta_{i+1}^* \leq \beta_{u,i+1}$, $$\beta_{i+1} = \beta_{i+1}^* \quad (34)$$

$$\alpha_{i+1} = \alpha_{i+1}^* \quad (35)$$

(d) In the case except for the above cases and when $\beta_{i+1}^* \geq \beta_{u,i+1}$, $$\beta_{i+1} = _{u,i+1} \quad (36)$$

$$\alpha_{i+1} = \frac{\gamma_{i+1}^*}{\beta_{u,i+1}} \quad (37)$$

(h) In the case of (d) and when $\alpha_{i+1}^* < \min \alpha$, $$\alpha_{i+1} = \min \alpha \quad (38)$$

$$\beta_{i+1} = \frac{\gamma_{i+1}^*}{\min \alpha} \quad (39)$$

(f) In the case except for the above cases, that is, when $\beta_{i+1}^* \leq \beta_{l,i+1}$, $$\beta_{i+1} = \beta_{l,i+1} \quad (40)$$

$$\alpha_{i+1} = \frac{\gamma_{i+1}^*}{\beta_{l,i+1}} \quad (41)$$

(g) In the case of (f) and when $\alpha_{i+1}^* > \max \alpha$, $$\alpha_{i+1} = \max \alpha \quad (42)$$

$$\beta_{i+1} = \frac{\gamma_{i+1}^*}{\max \alpha} \quad (43)$$

On the other hand, by changing the linear extrapolation by the expression (23) to the following expression (44), extrapolation by a two-dimensional curve can be used.

$$B_{i+1}^* = 3 \times (f_i \cdot A_i - f_{i-1} \cdot A_{i-1}) + f_{i-2} \cdot A_{i-2} \quad (44)$$

The reason why the setting values when the X-ray dose and the iris exceed the limit values of the apparatus, for example, (a) and (b) are set on a predetermined line on which the product of the X-ray dose and the iris is constant is because that deterioration of the picture quality of the image can be minimized as compared with the case of setting them to other values.

Figure 17:
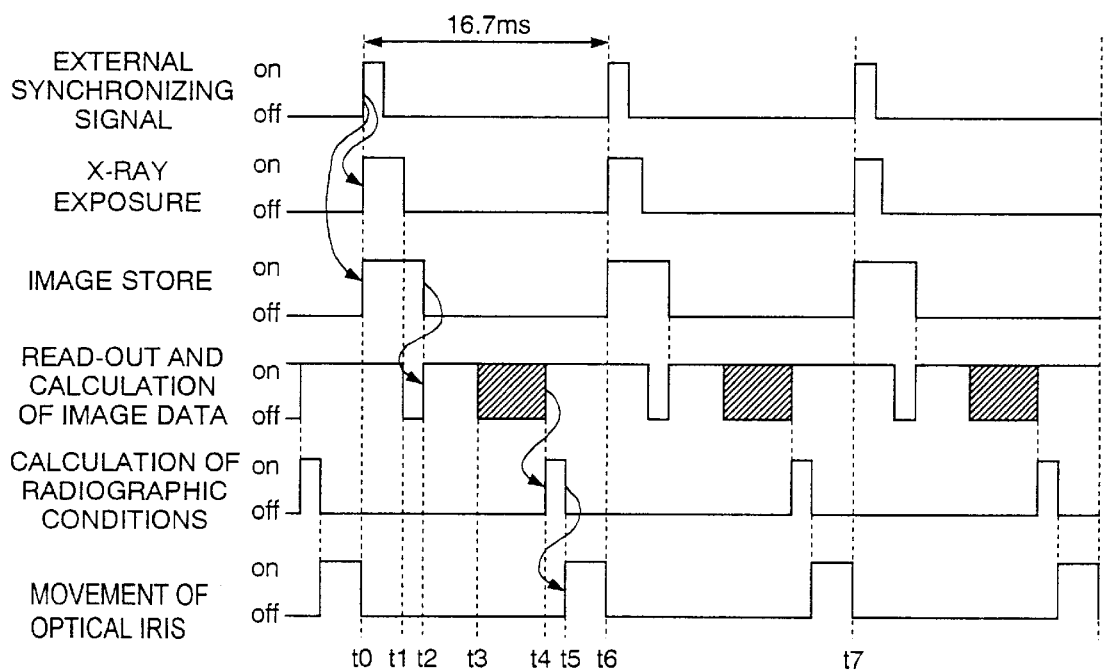
FIG. 17 is a diagram showing an example of a time sequence in the rotatographic apparatus according to the first embodiment.
Figure 18:
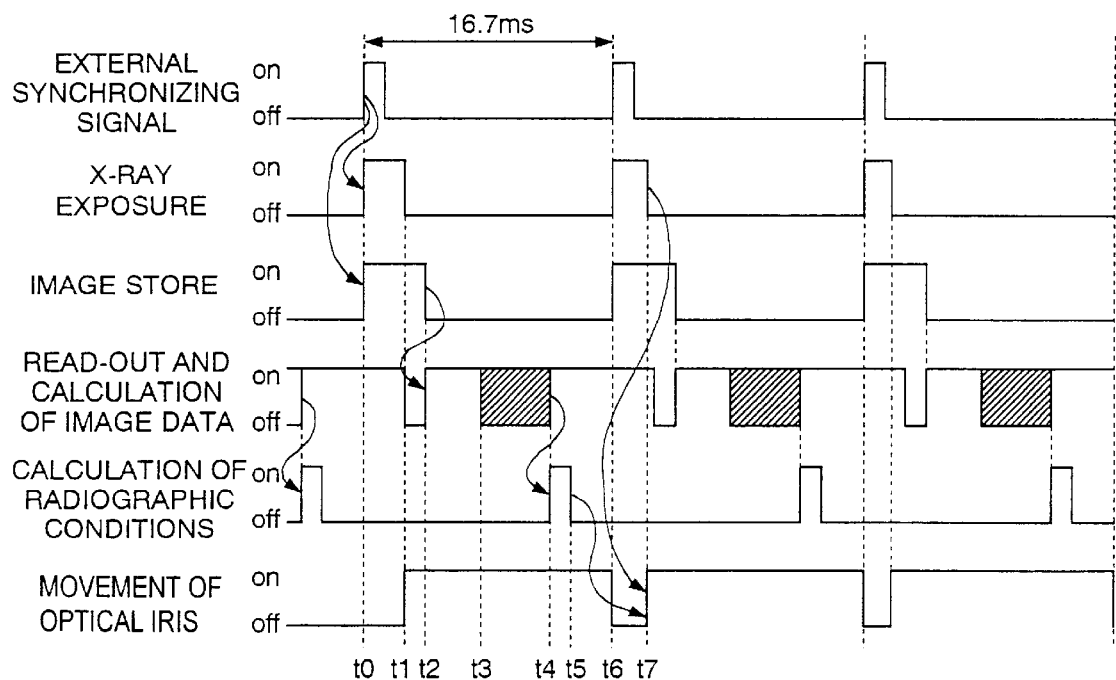
FIG. 18 is a diagram showing an example of the time sequence in the rotatographic apparatus according to the first embodiment.

FIGS. 17 and 18 are diagrams showing examples of time sequence in the rotatographic apparatus of the first embodiment. The radiographic operation of the rotatographic apparatus of the embodiment will be described hereinbelow with reference to FIGS. 17 and 18.

FIG. 17 is a diagram showing a time sequence at the time of ultrahigh-speed radiographic exposure. In this case, an external sync signal is supplied from the control circuit 102 for synchronized camera signal to the television camera 624 every 16.67 ms (described as 16.7 ms in FIG. 17) (t0). The X-ray radiation pulse (X-ray radiation in FIG. 17) is supplied from the controller 110 for external units synchronously with the external sync signal (t0). Simultaneously, the television camera 624 executes accumulation of images in the CCD (t0). The image accumulating time is set to a value equal to or larger than the maximum X-ray pulse width in the measurement on the basis of instruction from the PC 101 for control. When the accumulating operation to the CCD is finished (t2), reading operation of images from the CCD is started (t2). The reading operation of images from the CCD is performed, for example, from the upper part of the picture plane to the lower part. Hatched areas in the diagram show areas of image calculation which is executed simultaneously with image input (steps 801 to 805 in FIG. 14) (t3 to t4). The radiographic conditions are calculated by the DSP 108 (steps 806 and 807 in FIG. 14) (t4 to t5). When the calculation of the radiographic conditions is finished, the iris is moved (t5) and the movement is finished by the time when the external sync signal for the next frame is supplied (t6).

According to the sequence of FIG. 17 as mentioned above, since the X-ray pulse width and the iris for radiography in the next frame (t6 to t7) can be controlled in the period from t4 to t6, the ultrahigh-speed control is realized.

FIG. 18 is an example of a sequence in which the control in the sequence of FIG. 17 is executed every two frames. In the sequence, the control is executed with delay of one frame time. In the control shown in FIG. 18, reading and calculation of an image are executed simultaneously with the X-ray radiographic exposure for the next frame (t6 to t7).

(Second embodiment)

Figure 19:
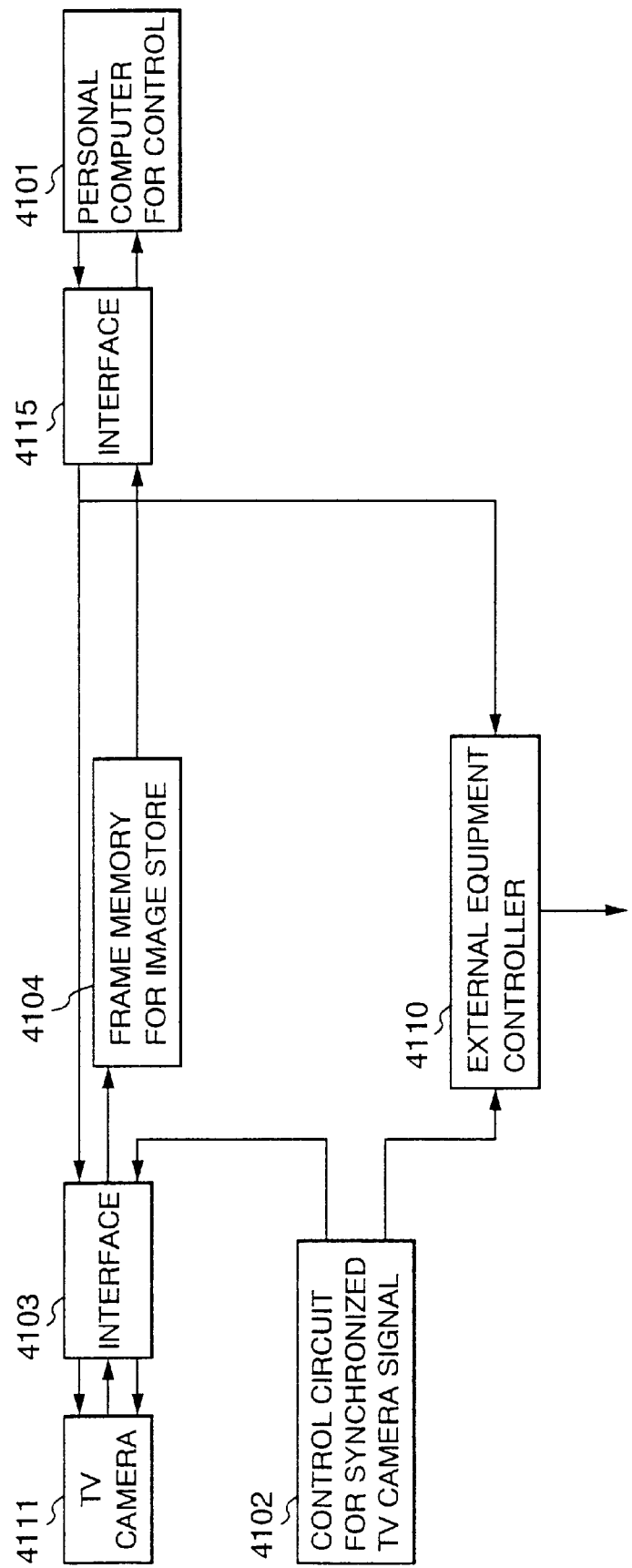
FIG. 19 is a block diagram illustrating a schematic construction of an image acquisition and quick control unit of a rotatographic apparatus as an X-ray apparatus of a second embodiment of the invention.

FIG. 19 is a block diagram for explaining a schematic construction of the image acquisition and quick control unit of the rotatographic apparatus serving as the X-ray apparatus according to the second embodiment of the invention. Reference numeral 4101 denotes a personal computer for control; 4102 a control circuit for synchronized camera signal; 4103 a camera interface; 4104 a frame memory for image storage; and 4110 a controller for external unit.

In the following description, only points different from the rotatographic apparatus of the first embodiment will be explained.

In the second embodiment, in order to set the X-ray relative noise of an aimed field in an X-ray transmission image obtained by the measurement almost equal to preset X-ray relative noise, X-ray transmission images from a plurality of directions are preliminarily acquired by preliminary radiographic exposure with small X-ray dose. The X-ray relative noise denotes the ratio of noise components to signal components of an X-ray image.

Under the direction conditions obtained by the preliminary radiographic exposure, the X-ray dose satisfying preset X-ray relative noise condition is calculated from the preliminarily acquired images and used. For direction conditions which were not obtained by the preliminary radiographic exposure, the X-ray dose is acquired by interpolating the conditions obtained from the preliminary radiographic exposure. A series of radiographic exposures are performed by controlling programs set in the PC 4101 for control under the obtained measurement conditions.

The operation of the image acquisition and quick control unit according to the second embodiment will be described with reference to FIG. 19.

Before or after the preliminary radiographic exposure, the X-ray noise relative level in the aimed pixel area in the main radiographic exposure, the maximum and minimum levels of the X-ray pulse width, and the maximum and minimum levels of the iris are set. The preliminary radiographic exposure is performed from a plurality of directions under the conditions of the constant X-ray dose, iris, and the gain of the amplifier.

The PC 4101 for control calculates both of maximum and minimum levels of the aimed area in the image acquired by the preliminary radiographic exposure. The X-ray conditions of the main radiographic exposure and the conditions of the iris under the same object conditions as those of the preliminary radiographic exposure (radiographic angles) are determined by calculation from the maximum and minimum levels, the X-ray dose for radiography, and the specification of the X-ray relative noise of the aimed area. With respect to the conditions which were not obtained from the preliminary radiographic exposure, the X-ray conditions of main radiographic exposure and the conditions of the iris are obtained by interpolation on the basis of the conditions obtained from the preliminary radiographic exposure.

With respect to all of the radiographic angle conditions for the main measurement, levels which can be realized are determined as the X-ray pulse width and the iris of the main measurement within the limit of the maximum and minimum levels of the X-ray pulse width and the maximum and minimum levels of the iris.

(Third embodiment)

Figure 20:
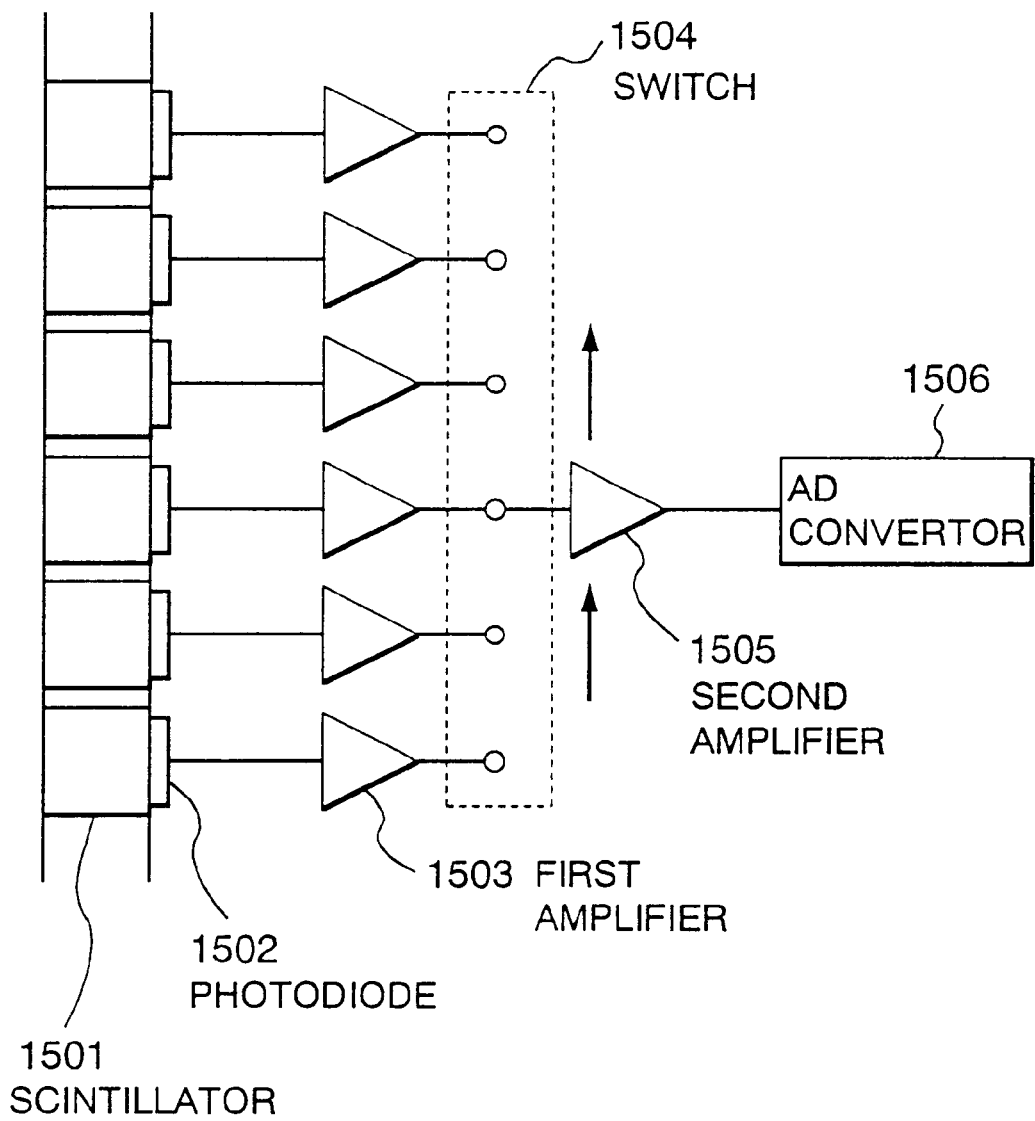
FIG. 20 is a diagram showing a schematic construction of an X-ray detector of a rotatographic apparatus according to a third embodiment of the invention.

FIG. 20 is a diagram showing a schematic construction of the X-ray detector of the rotatographic apparatus according to a third embodiment. The rotatographic apparatus of the third embodiment is different from the rotatographic apparatus of the first embodiment with respect to a point that the X-ray detector does not have an iris.

Reference numeral 1501 denotes scintillators; 1502 photo-diodes; 1503 first amplifiers; 1504 a switch; 1505 a second amplifier; and 1506 an AD converter.

In FIG. 20, the scintillator 1501 is a known scintillator and the photo-diode 1502 for detecting a light emitted by the scintillator 1501 is arranged on one side of the scintillator 1501.

The first amplifier 1503 is an amplifier at the first stage for converting resistance change of the photo-diode 1502 to change in output voltage and the output of the first amplifier 1503 is connected to the switch 1504. The first amplifiers 1503 are connected to the photo-diodes 1502 in a one-to-one manner.

The switch 1504 is a known switch for sequentially switching outputs of the first amplifiers 1503 and connecting the outputs to the input terminal of the second amplifier 1505.

The second amplifier 1505 is a known amplifier for amplifying the output of each first amplifier 1503 connected via the switch. The output of the second amplifier 1505 is connected to the AD converter 1506. The amplification factor of the second amplifier 1505 can be varied on the basis of the calculation result.

The optical iris is changed in the first embodiment. According to the rotatographic apparatus of the third embodiment, since the X-ray detector has no iris, the amplification factor (amplification gain) of the second amplifier 1505 is controlled in place of changing the iris. Therefore, since the limited dynamic range of the AD converter 1506 can be effectively used, the X-ray radiographic exposure having the wide dynamic range can be performed.

Although the amplification factor of the second amplifier 1505 is controlled in the third embodiment, the invention is not limited to the construction. For example, the amplification factors of the first amplification amplifiers 1505 or those of the first and second amplifiers 1503 and 1505 can be also controlled.

Except of the foregoing first to third embodiments, main items for determining the X-ray transmitted rate such as the width and the thickness in the depth direction of the object are preliminarily obtained by measurement other than the X-ray radiographic exposure and the program control of the X-ray dose under past similar conditions is applied as it is or the program can be also used by modifying a part.

Further, with respect to the setting of the calculation area E (m, n), for example, a target image is set on a three-dimensional image, coordinate position of the target in each projection data of rotatography is calculated, and the coordinate position can be set as a radiographic region which is desired to have high picture quality.

Although the predicted image $B_{i+1}^*$ is used as an image serving as a reference for obtaining the candidate $\alpha_{i+1}^*$ for X-ray pulse width and the candidate $\beta_{i+1}^*$ for iris by the DSP 108 in the embodiment, the invention is not limited to the image. For example, the image $A_i$ acquired just before or both of the image $A_i$ acquired just before and the image $A_{i-1}$ before the image $A_i$ can be used as reference. In this case, so-called a feedback control such that for example, the candidate $\alpha_{i+1}^*$ for X-ray pulse width and the candidate $\beta_{i+1}^*$ for iris are calculated from only the maximum and minimum levels of the image $A_i$ acquired just before, the value obtained by averaging the maximum and minimum levels of the image $A_i$ acquired just before and the image $A_{i-1}$ before the image $A_i$, respectively, or the like.

As another method, the candidate $\beta_{i+1}^*$ for X-ray pulse width and the candidate $\beta_{i+1}^*$ for iris can be also acquired on the basis of the measurement information obtained by directly measuring information regarding the X-ray transmitted rate such as the thickness and width of the object and the like and the transmitted rate obtained from X-ray images acquired in the past.

According to the embodiment, although the case of applying the invention to the typical X-ray rotatographic apparatus has been described, the invention is not limited to the case. For example, all or a part of the invention can be also applied to a fluoroscope and radiograph apparatus or an X-ray CT. For example, when the invention is applied to the fluoroscope and radiograph apparatus, by setting the aimed area in the center part of the axis of body of the object, the effects described in the first to third embodiments can be obtained. In case of applying the invention to the X-ray CT, by providing known reconstruction means for reading transmission images acquired from the periphery of the object from the frame memory 104 for image storage and reconstructing the transmission image, a CT image, that is, a slice image of the object can be reconstructed. With respect to the radiographic conditions and the like in this case, the X-ray CT image of the object can be reconstructed under the radiographic conditions described in the foregoing embodiments.

The X-ray rotatography to which the invention relates can be applied not only to a radiographic apparatus in which an X-ray tube and an X-ray image measurement unit which face each other rotate around an object, but also to a system in which the object lies on a rotation table, the X-ray tube and the X-ray image measurement unit face each other over the rotation table, and measurement is performed by rotating the rotation table on which the object lies or repeating rotation and stationary state of the rotation table step by step while the X-ray tube and the X-ray image measurement unit are in a stationary state. Such a rotation table type apparatus has an advantage that since the rotation unit is small, it can be easily and cheaply manufactured. Since the stationary state can be obtained at the time of measurement, there is an advantage that the radiographic image of an object who is not moved or deformed with time, which is not influenced by the imaging unit or motion of the object can be acquired with high resolution.

The invention achieved by the inventors for the second object of the invention has been specifically described on the basis of the foregoing embodiments. The invention, however, is not limited to the embodiments of the invention. It is obviously understood that the invention can be modified without departing from the gist of the invention.

The entire disclosures of Japanese Patent Applications No. 8-267518 and 9-004986 filed on Oct. 8, 1996 and Jan. 14, 1997, respectively, including specifications, claims, drawings and summaries are incorporated herein by reference in their entirety.

What is claimed is:

1. An x-ray apparatus comprising:

an X-ray tube for radiating X-rays;

an X-ray collimator for regulating an X-ray exposing area of an object;

an X-ray filter for changing energy spectrum of X-ray exposing the object and/or an X-ray grid for eliminating X-ray scattered when the X-ray transmits the object;

X-ray detection means for acquiring an X-ray image of the object;

display means for displaying the X-ray image;

storage means for storing a first function showing a relation among an averaged output value of the X-ray detection means and a tube voltage of the X-ray tube and a thickness of the object, wherein the relation is preliminarily measured in a state where predetermined values are, respectively, set to mAs value of the X-ray tube, the X-ray exposing area of the object, a distance between the object and an input face of the X-ray detection means, and a gain of the X-ray detection means, with respect to combinations of the plurality of X-ray filters and/or the plurality of X-ray grids, and for storing a second function showing a ratio of change in the averaged output values of the X-ray detection means preliminarily measured by setting change amounts of the X-ray exposing area of the object and the distance from the object to the input face of the X-ray detection means for predetermined values to variables, with respect to combinations of the plurality of X-ray filters and/or the plurality of X-ray grids;

radiographic conditions calculation means for calculating imaging conditions for radiography on the basis of imaging conditions for fluoroscopy and the first and second functions stored in the storage means; and control means for controlling the mAs value and the tube voltage of the x-ray tube and the gain of the X-ray detection means on the basis of the calculation result of the radiographic conditions calculation means.

2. The X-ray apparatus according to claim 1, wherein the radiographic conditions calculation means approximates the averaged output value of the X-ray detection means by a product of a ratio of the mAs value of the X-ray tube to the predetermined value for the mAs value of the X-ray tube, a ratio of the gain of the X-ray detection means to predetermined value for the X-ray detection means, the first function and the second function, and calculates the X-ray radiographic conditions from the product, the averaged output value of the X-ray detection means at the time of a fluoroscopic exposure, and the imaging conditions for fluoroscopy.

3. The X-ray apparatus according to claim 1, wherein the second function is a product of a third function and a fourth function, the third function shows a ratio of change in the averaged output values of the X-ray detection means when the change amount of the x-ray exposing area for the predetermined value is set to a variable, and the fourth function shows a ratio of change in the averaged output values of the X-ray detection means when the change amount of the distance from the object to the input face of the X-ray detection means for the predetermined value is set to a variable.

4. The X-ray apparatus according to claim 3, wherein the third function is a predetermined value.

5. The X-ray apparatus according to claim 3, wherein the fourth function is a predetermined value.

6. The X-ray apparatus according to claim 1, wherein when the tube voltage of the X-ray tube and/or the thickness of the object are set to variables of the second function, if a ratio of the change amount of the second function is equal to or larger than a predetermined value, the second function is corrected for the tube voltage of the X-ray tube and/or the thickness of the object.

7. The X-ray apparatus according to claim 1, wherein the radiographic conditions calculation means comprises:

average object thickness calculation means for approximating the averaged output value of the X-ray detection means by a product of a ratio of the mAs value of the X-ray tube to the predetermined value for the mAs value of the X-ray tube, a ratio of the gain of the X-ray detection means to predetermined value for the X-ray detection means, the first function and the second function, and for calculating a average thickness of the object from the product, the averaged output value of the X-ray detection means at the time of fluoroscopic exposure, and the fluoroscopic conditions; and means for calculating the radiographic conditions on the basis of the product and the average object thickness.

8. The X-ray apparatus according to claim 7, wherein the average object thickness calculation means comprises means for approximating the averaged output value of the X-ray detection means by a product of ratio of the mAs value of the X-ray tube to the predetermined value for the mAs value of the X-ray tube, a ratio of the gain of the X-ray detection means to the predetermined values for the gain of the X-ray detection means, the first function and second function, and for approximately calculating the average thickness of the object from the product and the fluoroscopic conditions.

9. The X-ray apparatus according to claim 1, wherein the radiographic conditions calculation means comprises:

tube saturation monitor means for monitoring whether the tube voltage and the mAs value of the X-ray tube and the gain of the X-ray detection means at the time of fluoroscopic exposure are within a preset permissible range or not; and output level corrector means for increasing the mAs value of the X-ray tube and/or the gain of the X-ray detection means at the time of radiographic exposure by predetermined times when the tube saturation monitor means determines that the tube voltage and the mAs value of the X-ray tube and the gain of the X-ray detection means are not included in the preset permissible range.

10. The X-ray apparatus according to claim 2, further comprising:

signal control means for setting an X-ray relative noise value on the basis of a maximum image level of a predetermined area in the X-ray image.

11. The X-ray apparatus according to claim 1, further comprising:

radiation dose control means for setting an X-ray relative noise value on the basis of a minimum image level of a predetermined area in the X-ray image.

12. The X-ray apparatus according to claim 1, wherein an X-ray relative noise value is set on the basis of a preliminary acquired X-ray image of the object.

13. The X-ray apparatus according to claim 1, wherein an X-ray relative noise value is set on the basis of information of the object acquired by measurement except for radiographic exposure and radiation dose of radiographic exposure executed in the past.

14. The X-ray apparatus according to claim 1, further comprising:

radiation dose control means for controlling an X-ray pulse width.

15. The X-ray apparatus according to claim 1, further comprising:

radiation dose control means for controlling the tube voltage of the X-ray tube.

16. The X-ray apparatus according to claims 1, further comprising:

rotation means for rotating the X-ray and the X-ray detection means around the object; and reconstruction means for reconstructing slice images of the object from the X-ray images.

17. The X-ray apparatus according to claim 2, further comprising:

signal control means for controlling an optical iris or an amplification gain of the X-ray detection means.

18. An X-ray apparatus comprising:

X-ray radiation means for radiating X-rays to an object;

imaging means for acquiring an X-ray image of the object;

X-ray image prediction means for forming a predicted X-ray image to be acquired next by using linear lines or two-or larger-dimensional curves on the basis of at least one X-ray image acquired just before forming the predicted X-ray image;

radiation dose control means for controlling a radiation dose so that the X-ray image having a predetermined X-ray relative noise value can be acquired on the basis of an image level of a predetermined area in the X-ray image; and signal control means for controlling an optical iris and/or an amplification gain of the imaging means so that an analog signal before being digitized in the imaging means is equal to or less than a predetermined value on the basis of the image level of the predetermined area in the X-ray image, wherein the radiation dose control means calculates a ratio of a first transformed level to a second transformed level, and calculates the radiation dose from a product of the ratio and an X-ray dose in a preset standard condition, the first transformed level is obtained by transforming a minimum image level of a predetermined area in the predicted X-ray image into the preset standard condition, and the second transformed level is obtained by transforming a minimum image level of the predetermined area in the X-ray image acquired already into the preset standard condition.

19. The X-ray apparatus according to claim 18, wherein the signal control means sets the X-ray relative noise value on the basis of a maximum image level of the predetermined area in the X-ray image.

20. The apparatus according to claim 18, further comprising:

rotation means for rotating the X-ray radiation means and the imaging means around the object; and reconstruction means for reconstructing a slice image of the object from the X-ray images.

21. An X-ray apparatus comprising:

X-ray radiation means for radiating X-rays to an object;

imaging means for acquiring an X-ray image of the object;

X-ray image prediction means for forming a predicted X-ray image to be acquired next by using linear lines or two-or larger-dimensional curves on the basis of at least one X-ray image acquired just before forming the predicted X-ray image; and radiation dose control means for controlling a radiation dose so that the X-ray image having a predetermined X-ray relative noise value can be acquired on the basis of an image level of a predetermined area in the predicted X-ray image, wherein the radiation dose control means controls an X-ray pulse width on the basis of a minimum image level of the predetermined area in the predicted X-ray image.

22. An X-ray apparatus comprising:

X-ray radiation means for radiating X-rays to an object;

imaging means for acquiring an X-ray image of the object;

X-ray image prediction means for forming a predicted X-ray image to be acquired next on the basis of at least one X-ray image acquired just before forming the predicted X-ray image; and radiation dose control means for controlling a radiation dose by controlling an X-ray pulse width on the basis of a minimum image level of the predetermined area in the predicted X-ray image.

23. An X-ray apparatus comprising:

X-ray radiation means for radiating X-rays to an object;

imaging means for acquiring an X-ray image of the object;

X-ray image prediction means for forming a predicted X-ray image to be acquired next by using linear lines or two-or larger-dimensional curves on the basis of at least one X-ray image acquired just before forming the predicted X-ray image; and signal control means for controlling an optical iris and/or an amplification gain of the imaging means so that an analog signal before being digitized in the imaging means is equal to or less than a predetermined value on the basis of an image level of a predetermined area in the predicted X-ray image, wherein signal control means controls the optical iris on the basis of a maximum image level of the predetermined area in the predicted X-ray image.

24. An X-ray apparatus comprising:

X-ray radiation means for radiating X-rays to an object;

imaging means for acquiring an X-ray image of the object;

X-ray image prediction means for forming a predicted X-ray image to be acquired next on the basis of at least one X-ray image acquired just before forming the predicted X-ray image; and signal control means for controlling an optical iris of the imaging means on the basis of a maximum image level of a predetermined area in the predicted X-ray image.

25. An X-ray apparatus comprising:

X-ray radiation means for radiating X-rays to an object;

imaging means for acquiring an X-ray image of the object;

X-ray image prediction means for forming a predicted X-ray image to be acquired next on the basis of at least one X-ray image acquired just before forming the predicted X-ray image;

radiation dose control means for controlling a radiation dose by controlling an X-ray pulse width on the basis of a minimum image level of a predetermined area in the predicted X-ray image; and signal control means for controlling an optical iris of the imaging means on the basis of a maximum image level of the predetermined area in the predicted X-ray image.

26. An X-ray apparatus comprising:

X-ray radiation means for radiating X-rays to an object;

imaging means for acquiring an X-ray image of the object;

X-ray image prediction means for forming a predicted X-ray image to be acquired next by using linear lines or two-or larger-dimensional curves on the basis of at least one X-ray image acquired just before forming the predicted X-ray image; and radiation dose control means for controlling a radiation dose so that the X-ray image having a predetermined X-ray relative noise value can be acquired on the basis of an image level of a predetermined area in the X-ray image, wherein the radiation dose control means calculates a ratio of a first transformed level to a second transformed level, and calculates the radiation dose from a product of the ratio and an X-ray dose in a preset standard condition, the first transformed level is obtained by transforming a minimum image level of a predetermined area in the predicted X-ray image into the preset standard condition, and the second transformed level is obtained by transforming a minimum image level of the predetermined area in the X-ray image acquired already into the preset standard condition.

27. The X-ray apparatus according to claim 26, further comprising permissible range storage means for storing a radiation dose which is within a permissible range in the X-ray apparatus, and storing a radiation dose which exceeds the permissible range, wherein when the calculated radiation dose value exceeds the permissible range, the radiation dose value stored in the permissible range storage means is used as the calculated radiation dose value.

28. The X-ray apparatus according to claim 26, wherein the radiation dose control means sets the X-ray relative noise value on the basis of the minimum image level of the predetermined area in the X-ray image.

29. The X-ray apparatus according to claim 26, wherein the X-ray relative noise value is set on the basis of a preliminary acquired X-ray image of the object.

30. The X-ray apparatus according to claim 26, wherein the X-ray relative noise value is set on the basis of information of the object acquired by measurement except for radiographic exposure and radiation dose of radiographic exposure executed in the past.

31. The X-ray apparatus according to claim 26, wherein the radiation dose control means controls an X-ray pulse width in the X-ray radiation means.

32. The X-ray apparatus according to claim 26, wherein the radiation dose control means controls an X-ray tube voltage in the X-ray radiation means.

33. The X-ray apparatus according to claim 26, further comprising:

rotation means for rotating the X-ray radiation means and the imaging means around the object; and reconstruction means for reconstructing a slice image of the object from the X-ray images.

34. An X-ray apparatus comprising:

X-ray radiation means for radiating X-rays to an object;

imaging means for acquiring an X-ray image of the object; and radiation dose control means for controlling a radiation dose so that the X-ray image having a predetermined X-ray relative noise value can be acquired on the basis of an image level of a predetermined area in the X-ray image, wherein the radiation dose control means calculates a ratio of a transformed level obtained by transforming a minimum image level of the predetermined area in the X-ray image into a preset standard condition to a standard minimum level in the X-ray image obtained in the preset standard condition, and calculates the radiation dose from a product of the ratio and an X-ray dose in the preset standard condition.

35. The X-ray apparatus according to claim 34, further comprising permissible range storage means for storing a radiation dose which is within a permissible range in the X-ray apparatus, and storing a radiation dose which exceeds the permissible range, wherein when the calculated radiation dose value is exceeds the permissible range, the radiation dose value stored in the permissible range storage means is used as the calculated radiation dose value.

36. The X-ray apparatus according to claim 34, further comprising:

rotation means for rotating the X-ray radiation means and the imaging means around the object; and reconstruction means for reconstructing a slice image of the object from the X-ray images.

* * * * *